(12) United States Patent
Lee et al.

(10) Patent No.: US 12,381,014 B2
(45) Date of Patent: Aug. 5, 2025

(54) METHOD FOR ENHANCING AN ACCURACY OF A BENIGN TUMOR DEVELOPMENT TREND ASSESSMENT SYSTEM

(71) Applicants: National Yang Ming Chiao Tung University, Taipei (TW); TAIPEI VETERANS GENERAL HOSPITAL, Taipei (TW)

(72) Inventors: Cheng-Chia Lee, Taipei (TW); Huai-Che Yang, Taipei (TW); Wen-Yuh Chung, Taipei (TW); Chih-Chun Wu, Taipei (TW); Wan-Yuo Guo, Taipei (TW); Wei-Kai Lee, Taipei (TW); Tzu-Hsuan Huang, Taipei (TW); Chun-Yi Lin, Taipei (TW); Chia-Feng Lu, Taipei (TW); Yu-Te Wu, Taipei (TW)

(73) Assignees: NATIONAL YANG MING CHIAO TUNG UNIVERSITY, Taipei (TW); TAIPEI VETERANS GENERAL HOSPITAL, Taipei (TW)

( * ) Notice: Subject to any disclaimer, the term of this patent is extended or adjusted under 35 U.S.C. 154(b) by 777 days.

(21) Appl. No.: 17/590,514

(22) Filed: Feb. 1, 2022

(65) Prior Publication Data
US 2022/0157472 A1    May 19, 2022

Related U.S. Application Data

(63) Continuation-in-part of application No. 16/939,881, filed on Jul. 27, 2020, now Pat. No. 11,475,563.

(30) Foreign Application Priority Data
Feb. 27, 2020   (TW) .................... 109106437

(51) Int. Cl.
*G06T 7/00*    (2017.01)
*G16H 30/20*   (2018.01)
(Continued)

(52) U.S. Cl.
CPC ........... *G16H 50/70* (2018.01); *G06T 7/0014* (2013.01); *G16H 30/20* (2018.01); *G16H 50/20* (2018.01);
(Continued)

(58) Field of Classification Search
CPC ........ G16H 50/70; G16H 30/20; G16H 50/20; G16H 80/00; G16H 30/40; G16H 40/67;
(Continued)

(56) References Cited

U.S. PATENT DOCUMENTS

2011/0003854 A1* 1/2011 Ponten .................... A61P 35/00
                                                    514/648
2011/0201928 A1* 8/2011 Duric .................... G06T 7/0014
                                                    600/438
(Continued)

FOREIGN PATENT DOCUMENTS

| CN | 105765629 A | 7/2016 |
| TW | I-667996 B | 8/2019 |

OTHER PUBLICATIONS

Ronneberger et al., "U-Net: Convolutional Networks for Biomedical Image Segmentation," International Conference on Medical image computing and computer-assisted intervention: Springer; 2015. p. 234-41, 8 pages.
(Continued)

*Primary Examiner* — Van D Huynh
(74) *Attorney, Agent, or Firm* — MUNCY, GEISSLER, OLDS & LOWE, P.C.

(57) ABSTRACT

A method for enhancing an accuracy of a benign tumor development trend assessment system includes: a first pro-
(Continued)

cessing procedure, an image captured before the treatment is inputted to and be processed by a server computing device of the benign tumor development trend assessment system to obtain a first processing result; a second processing procedure, the images captured before and in at least one period after the treatment are inputted to and processed by the server computing device to obtain a second processing result; a trend analyzing procedure, the trend analyzing module of the server computing device analyzes the first processing result, the second processing result and the trend pathways to obtain a tumor development trend result; and a storing procedure, the first processing result, the second processing result and the tumor development trend result are transformed to an individual trend pathway which is stored in the trend analyzing module.

10 Claims, 18 Drawing Sheets

(51) Int. Cl.
  *G16H 50/20* (2018.01)
  *G16H 50/70* (2018.01)
  *G16H 80/00* (2018.01)
(52) U.S. Cl.
  CPC ... *G16H 80/00* (2018.01); *G06T 2207/30096* (2013.01)
(58) Field of Classification Search
  CPC ......... G06T 7/0014; G06T 2207/30096; G06T 7/0016
  See application file for complete search history.

(56) References Cited

U.S. PATENT DOCUMENTS

| | | | | |
|---|---|---|---|---|
| 2013/0329973 | A1* | 12/2013 | Cao | G06T 7/0016 382/128 |
| 2015/0087957 | A1 | 3/2015 | Liu et al. | |
| 2019/0087954 | A1* | 3/2019 | Lloyd | G06T 7/0012 |
| 2021/0319906 | A1* | 10/2021 | Hafez | G16H 20/00 |
| 2022/0095977 | A1* | 3/2022 | Ancona | A61B 5/201 |
| 2024/0105333 | A1* | 3/2024 | Van Der Zaag | G16B 20/20 |

OTHER PUBLICATIONS

Guotai Wang et al., "Automatic Segmentation of Vestibular Schwannoma from T2-Weighted MRI by Deep Spatial Attention with Hardness-Weighted Loss," Medical Image Computing and Computer Assisted Intervention-MICCAI 2019, LNCS, vol. 11765, Oct. 10, 2019, pp. 264-272.

"AI Project's annual international seminar and results exhibition", Pervasive Artificial Intelligence Research Labs, Nov. 14-15, 2019, 18 pages.

Wu et al., "Artificial intelligence driven automatic tumor detection and follow up, and precision medicine model for acoustic neuroma" and English translation, Most AIBMRC, Ministry of Science and Technology, 3 pages, Nov. 14, 2019.

Langenhuizen Patrick P. J. H. et al., "Prediction of transient tumor enlargement using MRI tumor texture after radiosurgery on vestibular schwannoma", *Medical Physics*, (2020), vol. 47, No. 4, pp. 1692-1701.

Guotai Wang et al., "Automatic Segmentation of Vestibular Schwannoma from T2-Weighted MRI by Deep Spatial Attention with Hardness-Weighted Loss," arxiv.org, Cornell University Library, 201 Olin Library Cornell University Ithaca, NY 14853, Jun. 10, 2019 (9 pages).

Booth, T. C. et al., "Machine learning and glioma imaging biomarkers," *Clinical Radiology*, (2020), vol. 75, No. 1, Elsevier, Amsterdam, NL, pp. 20-32.

Office Action mailed Nov. 10, 2020 in TW Application No. 109106437 (7 pages).

Cheng-Chia Lee et al., "Applying artificial intelligence to longitudinal imaging analysis of vestibular schwannoma following radiosurgery," Scientific Reports, 11(1), Feb. 2021, 10 pages.

* cited by examiner

METHOD FOR ENHANCING AN ACCURACY OF A BENIGN TUMOR DEVELOPMENT TREND ASSESSMENT SYSTEM

CROSS REFERENCE TO RELATED APPLICATIONS

This application is a Continuation-In-Part (CIP) of an earlier filed, pending, application, having application Ser. No. 16/939,881 and filed on Jul. 27, 2020, which claims priority under 35 U.S.C. § 119(a) on Patent Application No(s). 109106437 filed in Taiwan, Republic of China on Feb. 27, 2020, the entire contents of which are hereby incorporated by reference.

BACKGROUND OF THE INVENTION

Field of Invention

The invention relates to a method for enhancing the accuracy of a benign tumor development trend assessment system, in particular, to a method for enhancing the accuracy of the system for assessing a benign tumor development trend before or after a radiation treatment to the benign tumor.

Related Art

Although the benign tumor would not metastasize from the primary site to other sites, the benign tumor would still progress and oppress the tissue near the benign tumor. The influence of the benign tumor would be different according to the primary site. For example, "vestibular schwannoma" ("VS", which is also called "acoustic neuromas") is a benign tumor of the nervous system. Vestibular schwannoma (VS) that originates from the Schwann cell sheath of vestibulocochlear nerves is the most common type of schwannomas. Although VS is a benign tumor of the nervous system, it causes damage to vestibular function and carries a high risk of deafness, tinnitus, dizziness and facial palsy by tumor progression or treatment.

Currently, there are many radiation treatments for treating the benign tumor, such as Gamma Knife radiosurgery (GKRS). GKRS is a safe and effective strategy to treat VSs with an over 90% long-term tumor control rate and a lower risk of treatment-related complications. However, a small percentage of patients still have some issues for GKRS treatment. One of the issues is the patients suffer from the treatment failure. Another issue for GKRS in VS is the presence of transient tumor growth, i.e., pseudo-progression, due to tumor swelling after GKRS. Over decades, this transient pseudo-progression can still only be differentiated from the actual tumor progression by the time interval. The tumor pseudo-progression typically occurs from 6 to 18 months after radiation treatment, and the actual tumor progression can be determined at least 2 years after radiation treatment. These issues described above only can be observed after radiation treatment. Therefore, it may cause psychological stress to the patients and the health care professionals. Moreover, recent methods could not provide different clinical advices according to different patients for increasing the efficacy of the treatment.

In addition, generally, tumor regions are manually contoured by experienced surgeons by repeatedly reviewing tumor images to measure the tumor volume before GKRS, so as to determine the treatment area and dose delivery. Although tumor contours are delineated by well-trained surgeons, subjective annotations are inevitable. Furthermore, the process is time consuming.

As mentioned above, in the currently conventional benign tumor treatment methods, tumor regions should be manually contoured by experienced surgeons with repeatedly reviewing tumor images before radiation treatment to determine the treatment area and dose delivery. Therefore, subjective annotations are inevitable. Moreover, the process is time consuming. Furthermore, it could not provide different clinical advices according to different patients for increasing the efficacy of the treatment except for radiation treatment. Thus, if there is a method that could assess the tumor response of a patient that against the radiation treatment by automatically analyzing the tumor image before the radiation treatment, and then advice the patient to do radiation treatment or other treatment (such as surgical treatment), it will be much helpful.

Accordingly, it is an urgent need to provide an assessment system that can automatically assess the tumor development trend according to the tumor images, and then the system can provide advice to the health care professionals according to the assessment result. The benign tumor development trend assessment system can provide better treatment methods according to different patients to increase the efficacy of the treatments, and thus avoid a bad result of the treatment which may cause the anxiety in patient and the psychological stress of the health care professionals.

In addition, it is an urgent need to provide a method for enhancing the accuracy of the assessment system that can automatically assess the tumor development trend.

SUMMARY OF THE INVENTION

In view of the foregoing objectives, the purpose of the invention is to provide a method for enhancing the accuracy of an assessment system that can automatically assess the tumor development trend according to the tumor images, and then the system can provide the various advices to the health care professionals according to the assessment result. The benign tumor development trend assessment system can provide better treatment methods according to different patients to increase the efficacy of the treatments. In addition, the system also can assess whether pseudo-progression would occur in the patient and let the patient know in advance. It is helpful to reduce the anxiety in patient and the psychological stress of the health care professionals.

To achieve the above objective, the invention provides a method for enhancing an accuracy of a benign tumor development trend assessment system. The benign tumor development trend assessment system comprises an image outputting device and a server computing device. The server computing device comprises a trend analyzing module, the trend analyzing module stores a plurality of trend pathways, the trend pathways are obtained by the trend analyzing module through analyzing a plurality of reference images. The image outputting device outputs an image captured from a benign tumor of a patient before a treatment and outputs an image captured from the benign tumor of the patient in at least one period after the treatment. The method comprises a first processing procedure, a second processing procedure, a trend analyzing procedure and a storing procedure. In the first processing procedure, the image captured before the treatment is inputted to the server computing device and is processed by the server computing device to obtain a first processing result. In the second processing procedure, the image captured before the treatment and the image capture in at least one period after the treatment are inputted to the server computing device, and the images are processed by the server computing device to obtain a second processing result. In the trend analyzing procedure, the trend analyzing module analyzes the first processing result, the second processing result and the trend pathways to obtain a tumor development trend result. In the storing procedure, the first processing result, the second processing result and the tumor development trend result are transformed to an individual trend pathway, and the trend analyzing module further stores the individual trend pathway.

In one embodiment, the method further comprises an adjusting procedure. In the adjusting procedure, the individual trend pathway is compared with the trend pathways to obtain an adjusting trend pathway.

In one embodiment, the image outputting device further outputs an image captured from the benign tumor of the patient in another period after the treatment.

In one embodiment, the method further comprises a third processing procedure and an accurate trend analyzing procedure. In the third processing procedure, the image captured in the another period after the treatment is inputted to the server computing device and the image is processed by the server computing device to obtain a third processing result. In the accurate trend analyzing procedure, the trend analyzing module analyzes the third processing result, the individual trend pathway and/or the adjusting trend pathway to obtain an accurate tumor development trend result.

In one embodiment, the images of the benign tumor are automatically detected and delineated by the benign tumor development trend assessment system to obtain volumes of the images of the benign tumor in the first processing procedure, the second processing procedure, or the third processing procedure, respectively.

In one embodiment, the images are captured from one patient.

In one embodiment, the images are 2D images and/or 3D images.

In one embodiment, the at least one period after the treatment is a plurality of periods, and at least one of the periods is partially overlapped with a recommend follow-up time point.

In one embodiment, the recommend follow-up time point is 6 months after the treatment, 12 months after the treatment, 18 months after the treatment, or 24 months after the treatment.

In one embodiment, a duration of the periods is 1 month, 2 months, 3 months, 4 months, 5 months, or 6 months.

As mentioned above, the benign tumor development trend assessment system of this invention can automatically assess the tumor development trend according to the tumor images, and then the system can provide the various advices to the health care professionals according to the assessment results. The benign tumor development trend assessment system can provide better treatment methods according to different patients to increase the efficacy of the treatments. In addition, the system also can be used to assess whether pseudo-progression would occur in the patient and let the patient know in advance. It is helpful to reduce the anxiety in patient and the psychological stress of the health care professionals. In addition, the method of this invention can enhance the accuracy of the said benign tumor development trend assessment system.

BRIEF DESCRIPTION OF THE DRAWINGS

FIG. 4A shows the schematic views of the first image and the second image. FIG. 4B shows the schematic views of the first adjusting image and the second adjusting image. FIG. 4C shows the schematic views of the first calibrating image and the second calibrating image. FIG. 4D shows the schematic views of the first local image and the second local image. FIG. 4E shows the schematic views of the first ROI image and the second ROI image.

FIG. 5A shows the three-dimensional scatter plots of tumor features of a plurality of reference images. FIG. 5B shows the predictive model scores transferred from the tumor features of FIG. 5A. FIG. 5C shows the resultant receiver operating characteristic curves for assessing "the benign tumor has non-response to the radiation treatment" or "the benign tumor has a response to the radiation treatment".

FIG. 6A shows the three-dimensional scatter plots of tumor features of a plurality of reference images. FIG. 6B shows the predictive model scores transferred from the tumor features of FIG. 6A. FIG. 6C shows the resultant receiver operating characteristic curves for assessing "the benign tumor has a response to the radiation treatment with pseudo-progression" or "the benign tumor has a response to the radiation treatment without pseudo-progression".

DETAILED DESCRIPTION OF THE INVENTION

Figure 1A:
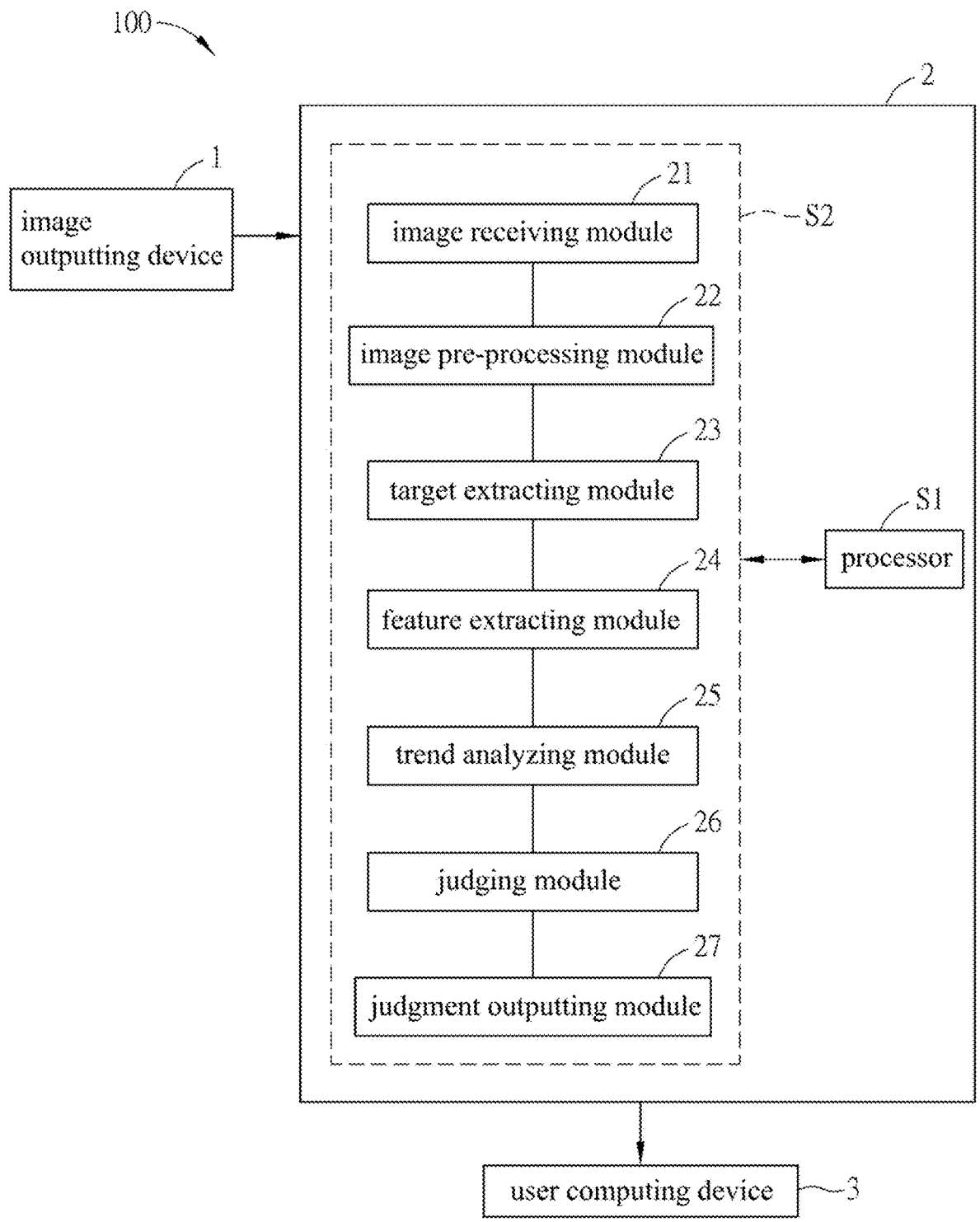
FIG. 1A is a schematic view of a preferred embodiment that showing the benign tumor development trend assessment system of this disclosure.
Figure 1B:
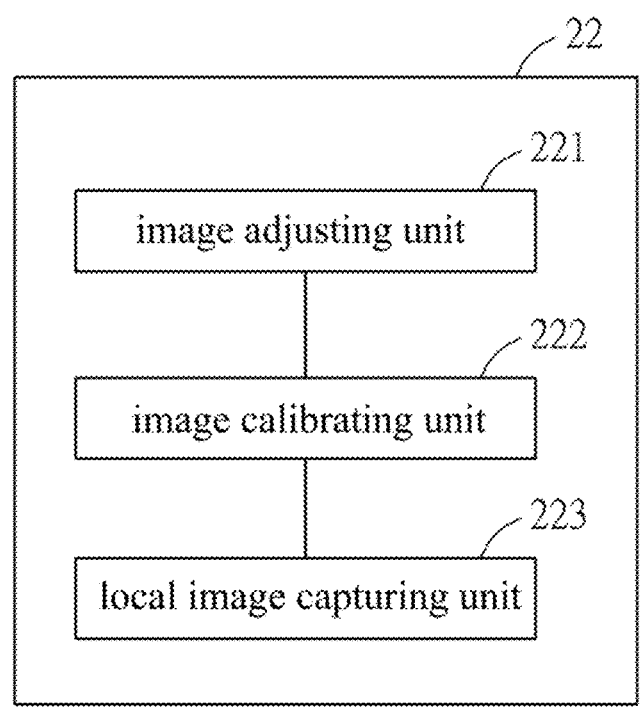
FIG. 1B is the schematic view of the image pre-processing module in FIG. 1A.

The embodiments and examples of the benign tumor development trend assessment system, server computing device thereof and computer readable storage medium in this invention will be apparent from the following detailed description, which proceeds with reference to the accompanying figures, wherein the same references relate to the same elements.

The benign tumor development trend assessment system of this invention can automatically assess the tumor development trend according to the tumor images, and then the system provides the various advices to the health care professionals according to the assessment results. The benign tumor development trend assessment system can provide better treatment methods according to different patients to increase the efficacy of the treatments. In addition, the system also can be used to assess whether pseudo-progression would occur in the patient and let the patient know in advance. It is helpful to reduce the anxiety in patient and the psychological stress of the health care professionals.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

As used herein, the term "benign tumor" refers to a tumor that does not metastasize from the primary site to other sites. The benign tumor is, for example but not limited to, acoustic neuromas, meningioma, pituitary tumor, cellular neuroma, or craniopharyngioma. As used herein, the term "benign tumor" is also called "tumor".

The term "tumor progression" refers to a tumor that keeps proliferation and getting bigger (keep getting bigger).

The term "pseudo-progression" refers to a tumor that swells after treatment and then regression (getting bigger and then getting smaller). Pseudo-progression is different from progression (keep getting bigger).

As used herein, the term "radiation treatment" refers to radiosurgery by using radioactive ray. For example but not limited to, Gamma Knife radiosurgery (GKRS), Cyber Knife radiosurgery, Photon Knife radiosurgery or other radiosurgery methods which the person in the art knows that can be used to treat the benign tumor.

The term "U-Net neural network" is also called "3D U-Net neural network" or "3D single pathway U-Net neural network". "U-Net neural network" is a kind of neural network derived from convolutional neural network (CNN), which is used for analyzing images, especially medical images. The examples of "U-Net neural network" which used for analyzing medical images please refer to Wang G et al., Automatic Segmentation of Vestibular Schwannoma from T2-Weighted MRI by Deep Spatial Attention with Hardness-Weighted Loss. arXiv preprint arXiv:190603906. 2019 and Ronneberger O et al., Convolutional networks for biomedical image segmentation. International Conference on Medical image computing and computer-assisted intervention: Springer; 2015. p. 234-41. "U-Net neural network" has 23 convolutional layers and pools 4 times. There is only one size of convolution kernels in a convolutional layer of "U-Net neural network" for the extraction of the features from medical images, for example but not limited to 3×3×3.

The term "3D dual-pathway U-Net neural network" is a kind of neural network modified from "U-Net neural network". In this embodiment, "3D dual-pathway U-Net neural network" has 10 convolutional layers and pools 2 times. There is two different sizes of convolution kernels in a convolutional layer of "3D dual-pathway U-Net neural network" for the extraction of the features from medical images, for example but not limited to 3×3×1 and 1×1×3. The kernel with 3×3×1 is for analyzing in-plane features of images (along the x-y axis of the image) while the kernel with 1×1×3 is for analyzing through-plane features from images (along the z axis of the image). Therefore, compared with "U-Net neural network", "3D dual-pathway U-Net neural network" is more accurate for analyzing medical images.

The terms "first" and "second" are used for the illustrative purpose only and cannot be understood as indicating or implying the relative importance or implicitly specifying the number of indicated technical features.

Please refer to FIG. 1A, FIG. 1A is a schematic view of a preferred embodiment that showing the benign tumor development trend assessment system of this disclosure. In this embodiment, the benign tumor development trend assessment system 100 comprises an image outputting device 1 and a server computing device 2.

Figure 4A:
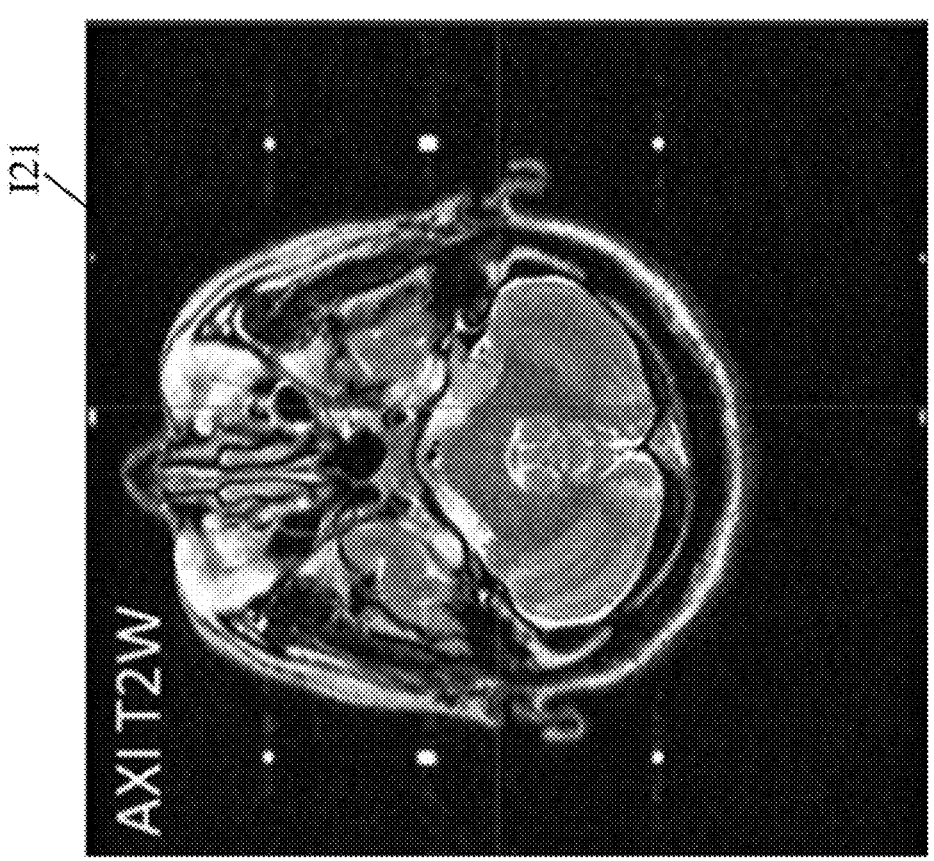
FIGS. 4A-4E are schematic views of the tumor images which are processed by the benign tumor development trend assessment system of this disclosure.
Figure 4A:
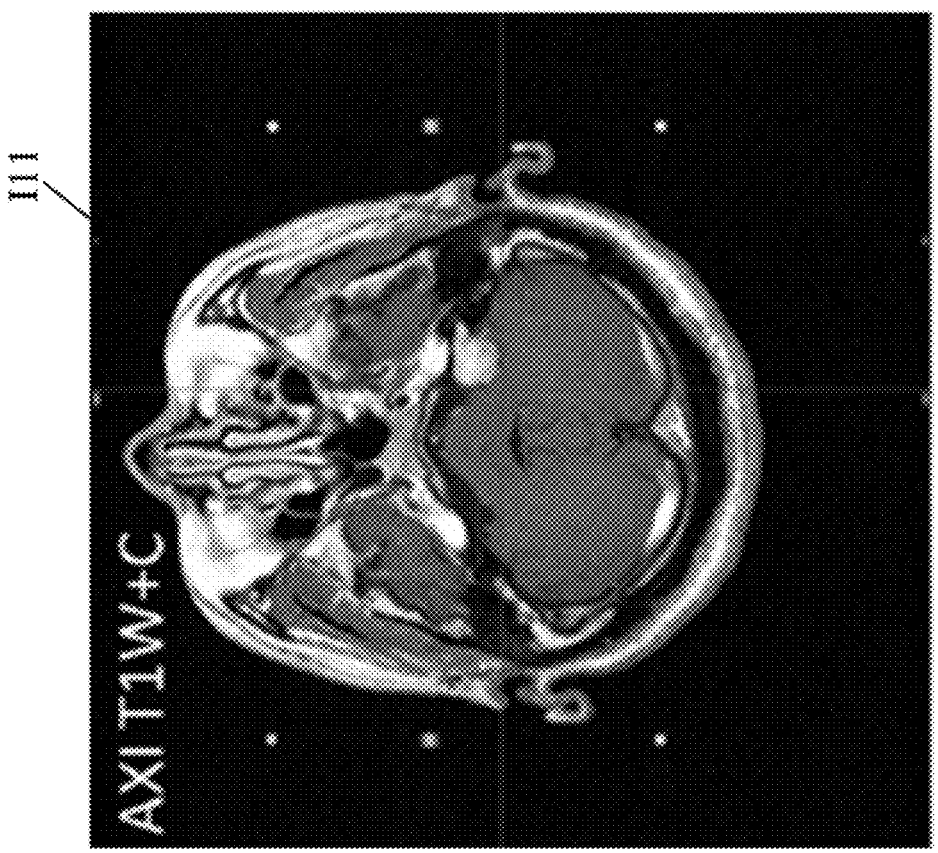

Please refer to FIGS. 1A and 4A, simultaneously. FIGS. 4A-4E are schematic views of the tumor images which are processed by the benign tumor development trend assessment system of this disclosure. FIG. 4A shows the schematic views of the first image and the second image. The image outputting device 1 outputs a first image I11 and a second image I21 captured from the same position in a benign tumor. The benign tumor is, for example but not limited to, acoustic neuromas, meningioma, pituitary tumor, cellular neuroma, or craniopharyngioma. The first image I11 and the second image I21 are the MRI images taken by magnetic resonance imaging (MRI) device. The contrast of the first image is different from that of the second image. In other words, the first image I11 and the second image I21 are captured from the same position of the benign tumor by MRI device by using different parameters. The images are, for example but not limited to, T1-weighted (T1 W) image, T2-weighted (T2 W) image, or T1-weighted gadolinium contrast enhanced (T1W+C) image. For example, the first image I11 and the second image I21 may be T1W images, T2 W images, or T1W+C images, and the first image I11 and the second image I21 are different images. In other words, when the first image I11 is T1W image, the second image I21 is T2 W image or T1W+C image; when the first image I11 is T2 W image, the second image I21 is T1 W image or T1 W+C image; when the first image I11 is T1W+C image, the second image I21 is T1 W image or T2 W image. Preferably, the first image I11 is T1W+C image, and the second image I21 is T2 W image.

As shown in FIG. 1A, in this embodiment, the server computing device 2 comprises an image receiving module 21, an image pre-processing module 22, a target extracting module 23, a feature extracting module 24 and a trend analyzing module 25.

Figure 4B:
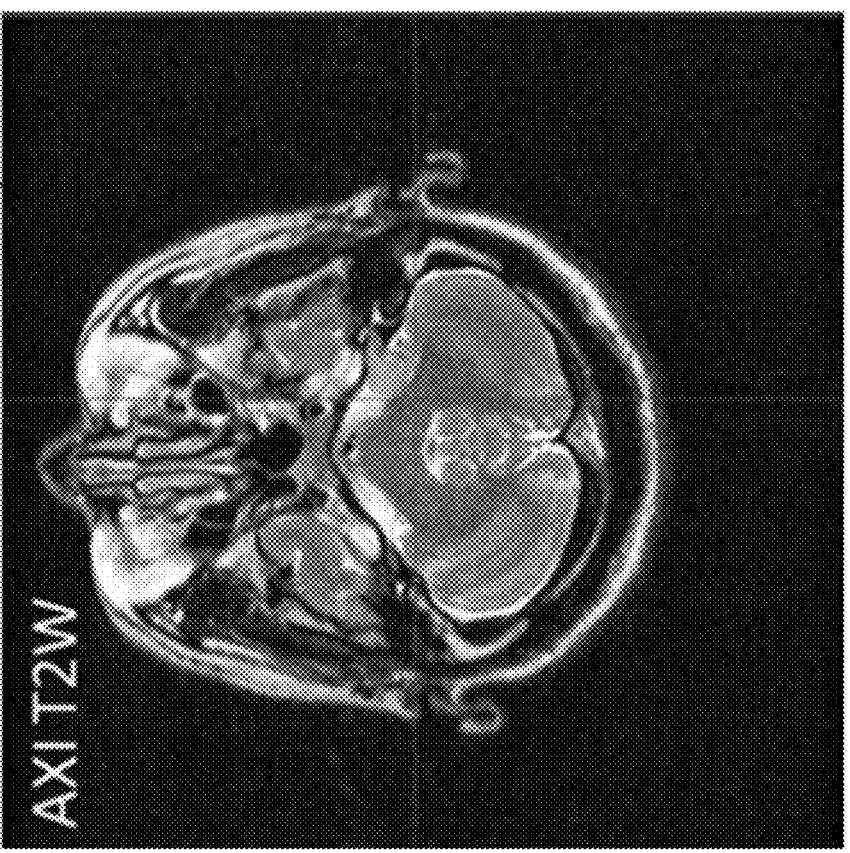
Figure 4B:
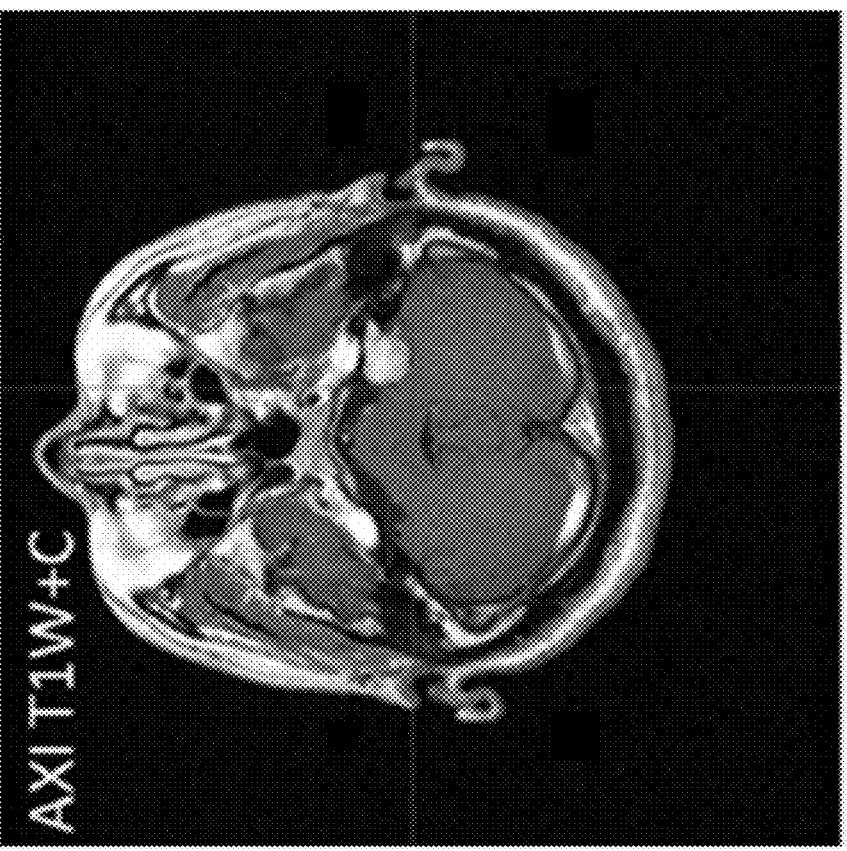
Figure 4C:
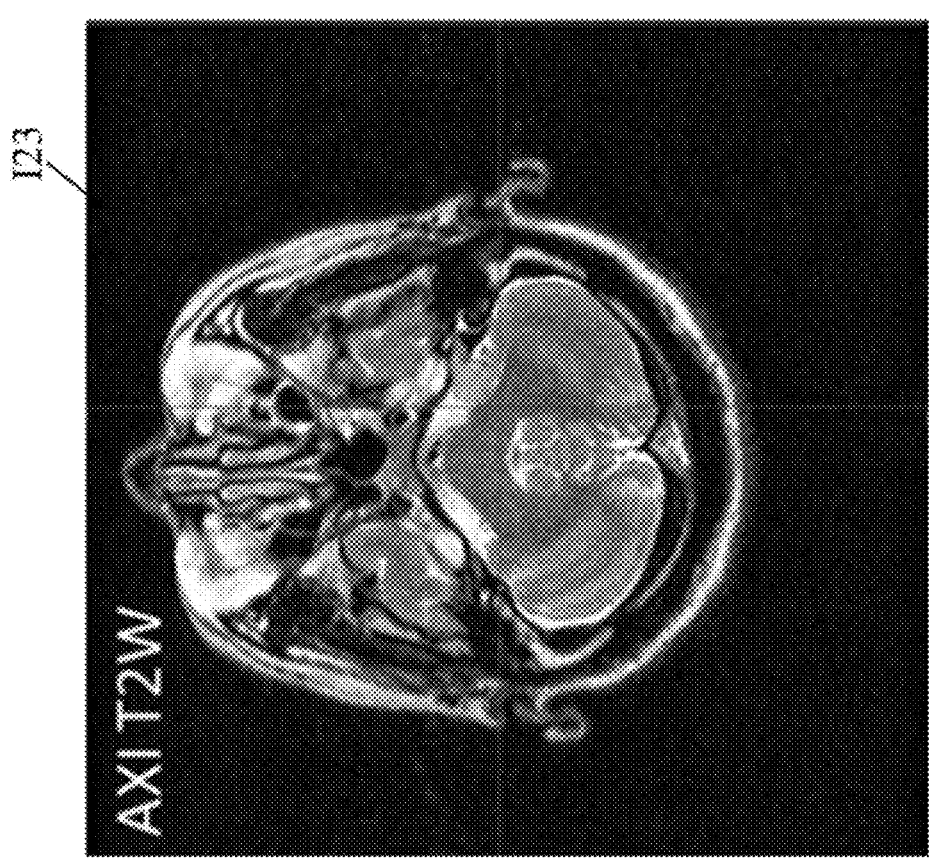
Figure 4C:
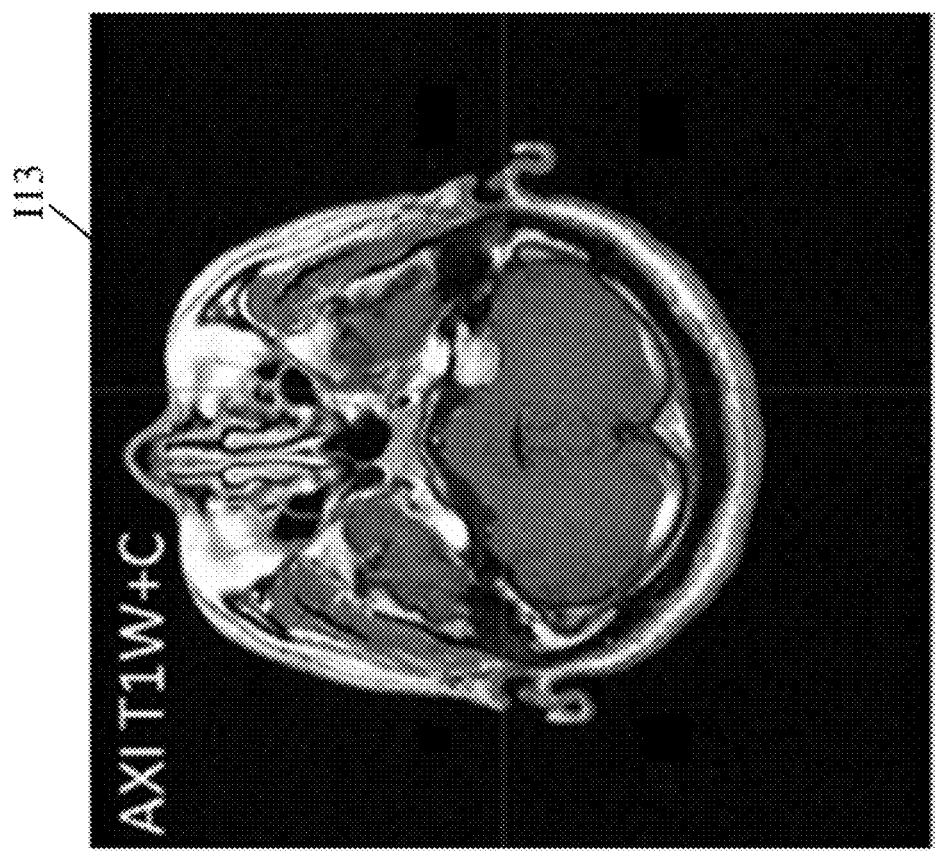
Figure 4D:
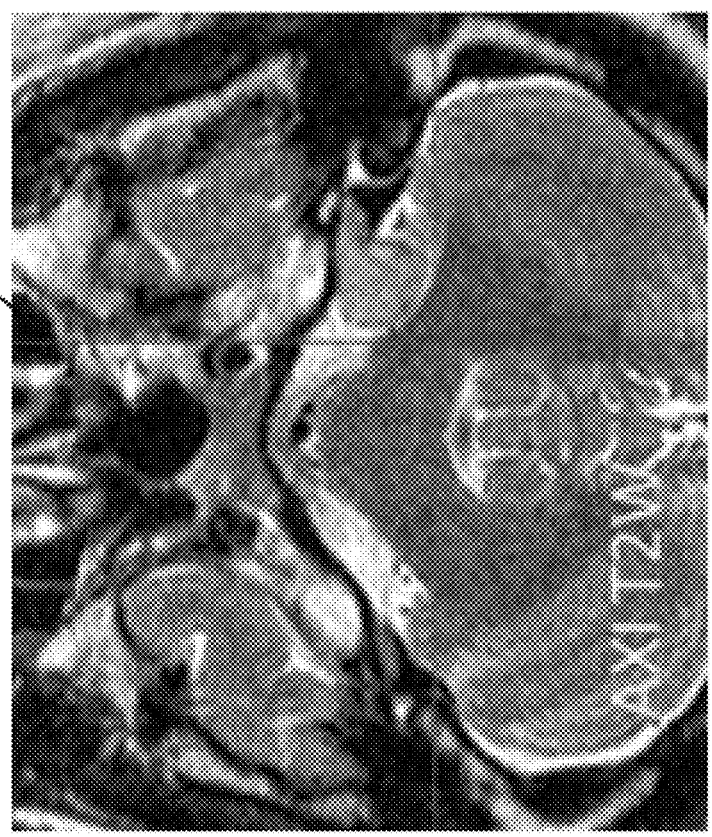
Figure 4D:
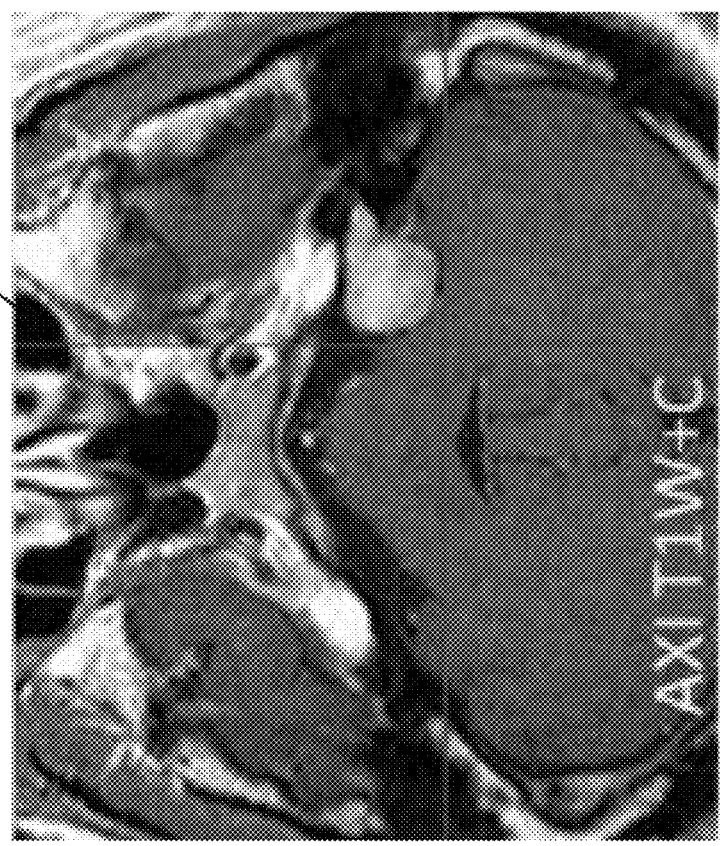
Figure 4E:
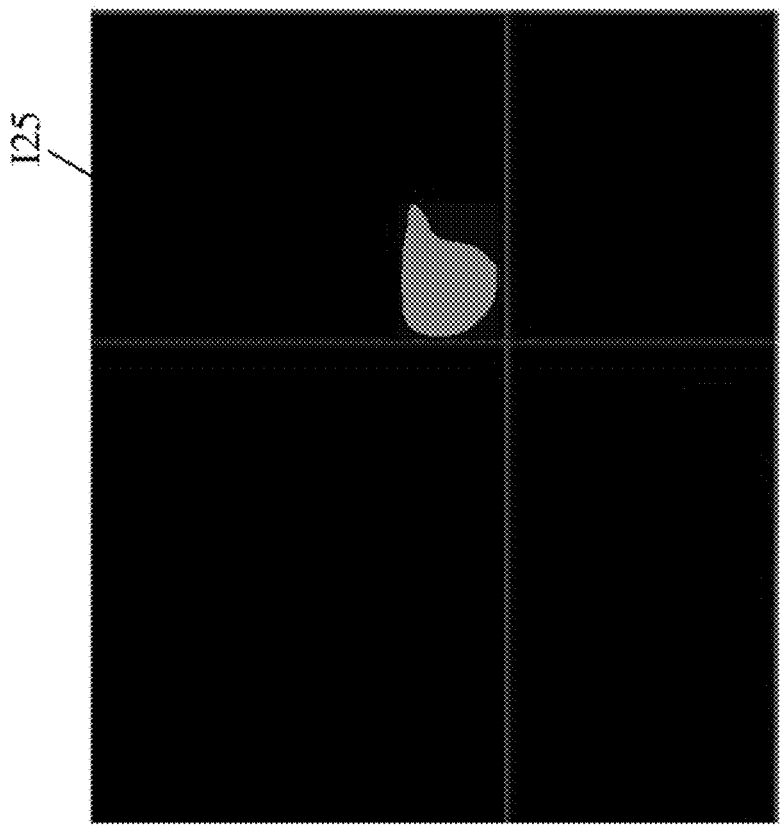
Figure 4E:
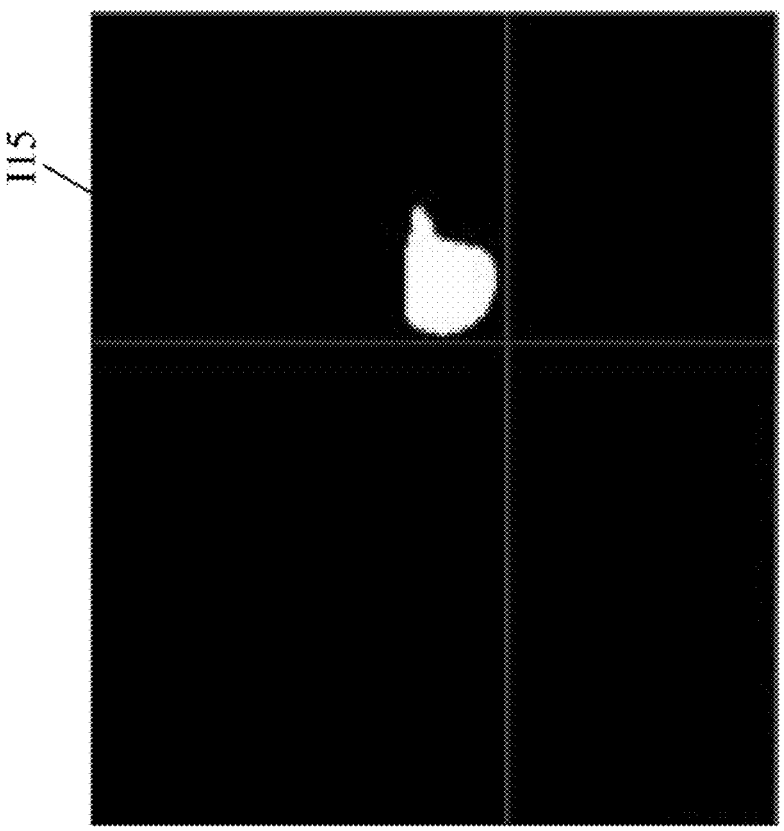

Please refer to FIGS. 1A and 4A-4E at the same time to explain the functions of each module. FIG. 4B shows the schematic views of the first adjusting image and the second adjusting image. FIG. 4C shows the schematic views of the first calibrating image and the second calibrating image. FIG. 4D shows the schematic views of the first local image and the second local image. FIG. 4E shows the schematic views of the first ROI image and the second ROI image.

As shown in FIGS. 1A and 4A, the image receiving module 21 receives the first image I11 and the second image I21 outputted by the image outputting device 1.

As shown in FIGS. 1A, 1B, and 4A-4D, FIG. 1B is the schematic view of the image pre-processing module in FIG. 1A. The image pre-processing module 22 pre-processes the first image I11 and the second image I21 to obtain a first local image I14 and a second local image I24, respectively. In more detailed, please refer to FIGS. 1A-1B, the image pre-processing module 22 comprises an image adjusting unit 221, an image calibrating unit 222 and a local image capturing unit 223. The image adjusting unit 221 adjusts the brightness and the resolution of the first image I11 and the brightness and the resolution of the second image I21, as well as removes the background of the first image I11 and the background of the second image I21 to obtain a first adjusting image I12 and a second adjusting image I22, respectively. The image calibrating unit 222 calibrates the position of the second adjusting image I22 by using the first adjusting image I12 to obtain a first calibrating image I13 and a second calibrating image I23. The local image capturing unit 223 captures a local image of the first calibrating image I13 and a local image of the second calibrating image I23 to obtain the first local image I14 and the second local image I24, respectively. In other words, image pre-processing module 22 adjusts the brightness and the resolution of the first image I11 and the brightness and the resolution of the second image I21, and then removes the background (such as position point or mask) of the first image I11 and the background of the second image I21. Then, the position of one of the images is calibrated by the image pre-processing module 22 using another image. After the adjustments of the brightness, the resolution and the positions of two images are completed, the local images of the benign tumor (includes the image of the tissue near the benign tumor) are captured to obtain the first local image I14 and the second local image I24.

As shown in FIGS. 1A and 4D-4E, the target extracting module 23 automatically detects and delineates a tumor region from the first local image I14 and the second local image I24 to obtain a first region of interest (ROI) image I15 and a second ROI image I25, respectively. For example, the target extracting module 23 automatically detects and delineates a tumor region from the first local image I14 and the second local image I24 through CNN. Preferably, the target extracting module 23 automatically detects and delineates a tumor region from the first local image I14 and the second local image I24 by using other methods based on CNN which can automatically detects and delineates a tumor region from images, for example but not limited to, U-Net neural network (3D single pathway U-Net neural network), or 3D dual-pathway U-Net neural network. Preferably, the target extracting module 23 automatically detects and delineates a tumor region from the first local image I14 and the second local image I24 by using 3D dual-pathway U-Net neural network.

The feature extracting module 24 automatically identifies the first ROI image I15 and the second ROI image I25 to obtain at least one first feature and at least one second feature, respectively. The at least one first feature is, for example but not limited to, a texture feature, or a grayscale feature, or texture feature and grayscale feature. The at least one second feature is, for example but not limited to, a texture feature, or a grayscale feature, or texture feature and grayscale feature. Texture features and grayscale features include, for example but not limited to, mean of local binary patterns (Mean of LBP), Long Run Low Gray-Level Emphasis (LRLGLE), skewness, standard deviation, and root mean square of the first ROI image and the second ROI image. Wherein the "Mean of LBP" are obtained from the analyses for the first ROI image and the second ROI image by using LBP filter. The "LRLGLE" are obtained from the analyses for the first ROI image and the second ROI image by using gray-level run-length matrix (GLRLM) filter. The "skewness", "standard deviation" and "root mean square" are obtained from the analyses for the first ROI image and the second ROI image by using histogram filter. For example, the feature extracting module 24 may automatically identifies the first ROI image I15 and the second ROI image I25 by using different filters through CNN, respectively, and then obtains at least one first feature and at least one second feature, respectively. Preferably, the feature extracting module 24 may automatically identify the first ROI image I15 and the second ROI image I25 by using different filters through other methods based on CNN which can automatically identify the first ROI image I15 and the second ROI image I25, for example but not limited to, 3D single pathway U-Net neural network, or 3D dual-pathway U-Net neural network. Preferably, the feature extracting module 24 automatically identify the first ROI image I15 and the second ROI image I25 by using different filters through 3D dual-pathway U-Net neural network.

The trend analyzing module 25 analyzes the at least one first feature and the at least one second feature to obtain a tumor development trend result for judging the tumor development trend. The first image and the second image may be the images before or after a radiation treatment. When the first image and the second image are the images before the radiation treatment, the tumor development trend result may be a prediction that the benign tumor has non-response to the radiation treatment or a prediction that the benign tumor has a response to the radiation treatment. When the first image and the second image are the images after the radiation treatment, the tumor development trend result may be a determination that the benign tumor has non-response to the radiation treatment or a determination that the benign tumor has a response to the radiation treatment. When the tumor development trend result is that the benign tumor has a response to the radiation treatment, the benign tumor has a response to the radiation treatment is that the benign tumor has a response to the radiation treatment with pseudo-progression or the benign tumor has a response to the radiation treatment without pseudo-progression. Herein, "the benign tumor has non-response to the radiation treatment" or "the benign tumor has a response to the radiation treatment" means that to predict/judge whether the size of the benign tumor changes (includes getting bigger and getting smaller) after the radiation treatment. If the size of the benign tumor changes (includes getting bigger and getting smaller) after the radiation treatment, the tumor development trend would be "the benign tumor has a response to the radiation treatment"; if the size of the benign tumor does not change after the radiation treatment, the tumor development trend would be "the benign tumor has non-response to the radiation treatment". When the tumor development trend result is that the benign tumor has a response to the radiation treatment (includes getting bigger and getting smaller), the benign tumor has a response to the radiation treatment is that the benign tumor has a response to the radiation treatment with pseudo-progression (getting bigger and then getting smaller) or the benign tumor has a response to the radiation treatment without pseudo-progression (getting smaller). For example, the trend analyzing module 25 analyzes the at least one first feature and the at least one second feature through, for example but not limited to, support vector machine (SVM), manual, or "gap analysis", and then obtains a tumor development trend result.

Preferably, the trend analyzing module 25 analyzes the at least one first feature and the at least one second feature through SVM. In this embodiment, the trend analyzing module 25 may stores a plurality of trend pathways. The trend analyzing module 25 analyzes the at least one first feature, the at least one second feature as well as the trend pathways. The trend pathways are obtained by the trend analyzing module 25 through analyzing the reference images. In more detailed, the benign tumor development trend assessment system may include a plurality of reference images. These reference images may be stored in a database or the trend analyzing module 25. The trend analyzing module 25 analyzes the reference images through, for example but not limited to, SVM, to obtain a plurality of trend pathways. Then, the trend pathways are stored in the trend analyzing module 25. When the trend analyzing module 25 analyzes the at least one first feature and the at least one second feature through, for example but not limited to, SVM, it analyzes the at least one first feature, the at least one second feature as well as the trend pathways to find out which one of the trend pathways is coincided with these features. The brief process is described as followed, and it will be omitted here.

Please refer to FIGS. 1A and 4A, in this embodiment, the server computing device 2 may further comprises a judging module 26. The judging module 26 generates a judgment according to the tumor development trend result. In another embodiment, the server computing device 2 may further comprises a judgment outputting module 27. The judgment outputting module 27 outputs the judgment. In more detailed, the first image I11 and the second image I21 may be the images before or after a radiation treatment. When the first image I11 and the second image I21 are the images before the radiation treatment and the tumor development trend result is a prediction that the benign tumor has non-response to the radiation treatment, the judgment is to do other treatments. When the first image I11 and the second image I21 are the images before the radiation treatment and the tumor development trend result is a prediction that the benign tumor has a response to the radiation treatment (including the benign tumor has a response to the radiation treatment with pseudo-progression as well as the benign tumor has a response to the radiation treatment without pseudo-progression), the judgment is to do the radiation treatment. When the first image I11 and the second image I21 are the images after the radiation treatment and the tumor development trend result is a determination that the benign tumor has non-response after the radiation treatment, the judgment is to do other treatments. When the first image I11 and the second image I21 are the images after the radiation treatment and the tumor development trend result is a determination that the benign tumor has a response to the radiation treatment (including the benign tumor has a response to the radiation treatment with pseudo-progression as well as the benign tumor has a response to the radiation treatment without pseudo-progression), the judgment is to follow-up.

Please refer to FIG. 1A, in this embodiment, the server computing device 2 may further comprises a processor S1. The processor S1 executes the image receiving module 21, the image pre-processing module 22, the target extracting module 23, the feature extracting module 24, the trend analyzing module 25, the judging module 26 and the judgment outputting module 27 to execute the procedures as described above.

Please refer to FIG. 1A, in this embodiment, the benign tumor development trend assessment system 100 may further comprises a user computing device 3. The user computing device 3 receives the judgment outputted by the server computing device 2.

Figure 2:
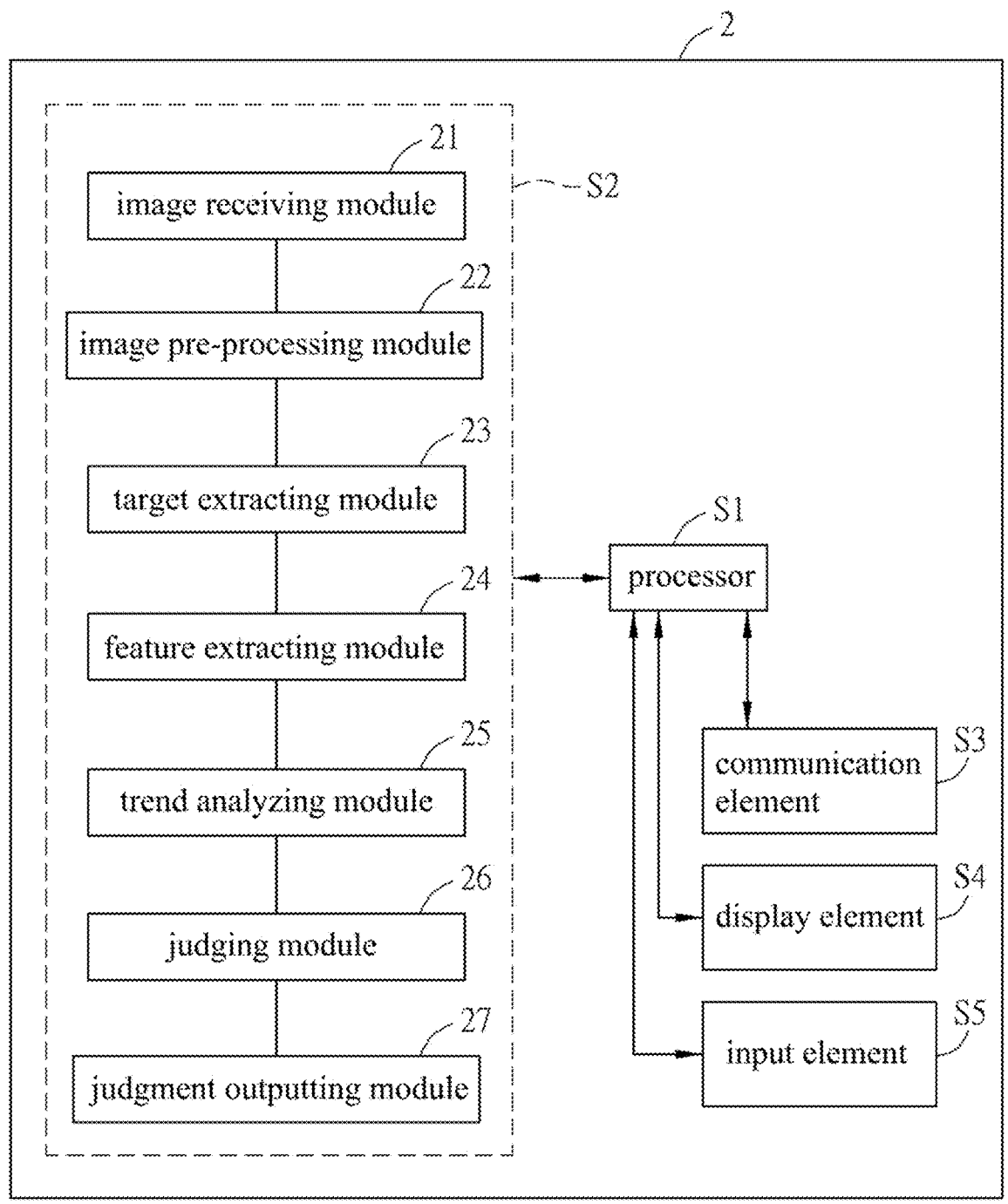
FIG. 2 is a schematic view showing the server computing device of the benign tumor development trend assessment system of this disclosure.

Please refer to FIGS. 2 and 1A, simultaneously. FIG. 2 is a schematic view showing the server computing device of the benign tumor development trend assessment system of this disclosure. A server computing device 2 is applied in a benign tumor development trend assessment system 100. The benign tumor development trend assessment system 100 comprises an image outputting device 1 and the server computing device 2. The server computing device 2 comprises the above-mentioned modules, the procedures which these modules process and the functions of these modules are described above and that will be omitted here.

As shown in FIG. 2, the server computing device 2 may further comprises a computer readable storage medium S2, a communication element S3, a display element S4, an input element S5 and a housing (not shown). The server computing device 2 may be a server, a mobile phone, a panel, a laptop computer, a desk computer or other computer device. The server, the mobile phone, the panel, the laptop computer and the desk computer include a housing for accommodating the processor S1, the computer readable storage medium S2 and the communication element S3. The display element S4 and the input element S5 of the mobile phone, the panel and the laptop computer are disposed on the housing. The display element S4 and the input element S5 are individual devices connected to the server and the desk computer.

The processor S1 is coupled with the computer readable storage medium S2, the communication element S3, the display element S4, and the input element S5, and such configuration is used to execute the image receiving module 21, the image pre-processing module 22, the target extracting module 23, the feature extracting module 24, the trend analyzing module 25, the judging module 26 and the judgment outputting module 27 as the above-mentioned. The processor S1 is, for example, a processor for executing the modules (e.g. modules, program codes or instructions). The server computing device 2 may include one or more processors S1, and the processor S1 can be a single-core or multi-core processor. The computer readable storage medium S2 can include any storage medium such as a random access memory or a non-volatile computer readable storage medium (e.g. a hard disk, a solid state disk (SSD), a flash memory, etc.) which stores the modules (e.g. modules, program codes or instructions) that can be executed by the processor S1. The modules (e.g. modules, program codes or instructions) can be loaded into the random access memory from the non-volatile computer readable storage medium and executed by the processor S1. The communication element S3 can be a device that can provide a network connection, for example, a network card, a network chip, a modem and the likes. The display element S4 includes a display card, a display chip, a display device, and the likes. The input element S5 can be, for example, a keyboard, a mouse, or a touch screen, etc.

The above embodiments are illustrations that the image receiving module 21, the image pre-processing module 22, the target extracting module 23, the feature extracting module 24, the trend analyzing module 25, the judging module 26 and the judgment outputting module 27 are stored in the computer readable storage medium S2 as software and executed by the processor S1 of the computer device. Alternatively, the image receiving module 21, the image pre-processing module 22, the target extracting module 23, the feature extracting module 24, the trend analyzing module 25, the judging module 26 and the judgment outputting module 27 may also be stored in the random access memory of the processor S1 as software (not shown). Alternatively, the image receiving module 21, the image pre-processing module 22, the target extracting module 23, the feature extracting module 24, the trend analyzing module 25, the judging module 26 and the judgment outputting module 27 may be coupled with the processor S1 (not shown) as hardware (for example but not limited to, application specific integrated circuit, ASIC) and executed by the processor S1. Alternatively, the image receiving module 21, the image pre-processing module 22, the target extracting module 23, the feature extracting module 24, the trend analyzing module 25, the judging module 26 and the judgment outputting module 27 may be firmware such as the software of ASIC (not shown). The present invention is not limited by these disclosures.

In addition, the user computing device 3 may also comprises a processor, a computer readable storage medium, a communication element, a display element, an input element and a housing (not shown). The user computing device 3 may be a mobile phone, a panel, a laptop computer, a desk computer or other computer device. The mobile phone, the panel, the laptop computer and the desk computer include a housing for accommodating the processor, the computer readable storage medium and the communication element. The display element and the input element of the mobile phone, the panel and the laptop computer are disposed on the housing. In the desk computer, the display element and the input element are individual devices connected to the desk computer. The user computing device 3 and the server computing device 2 can be communicatively connected through, for example but not limited to, a network for receiving the judgment outputted by the server computing device 2.

Figure 3:
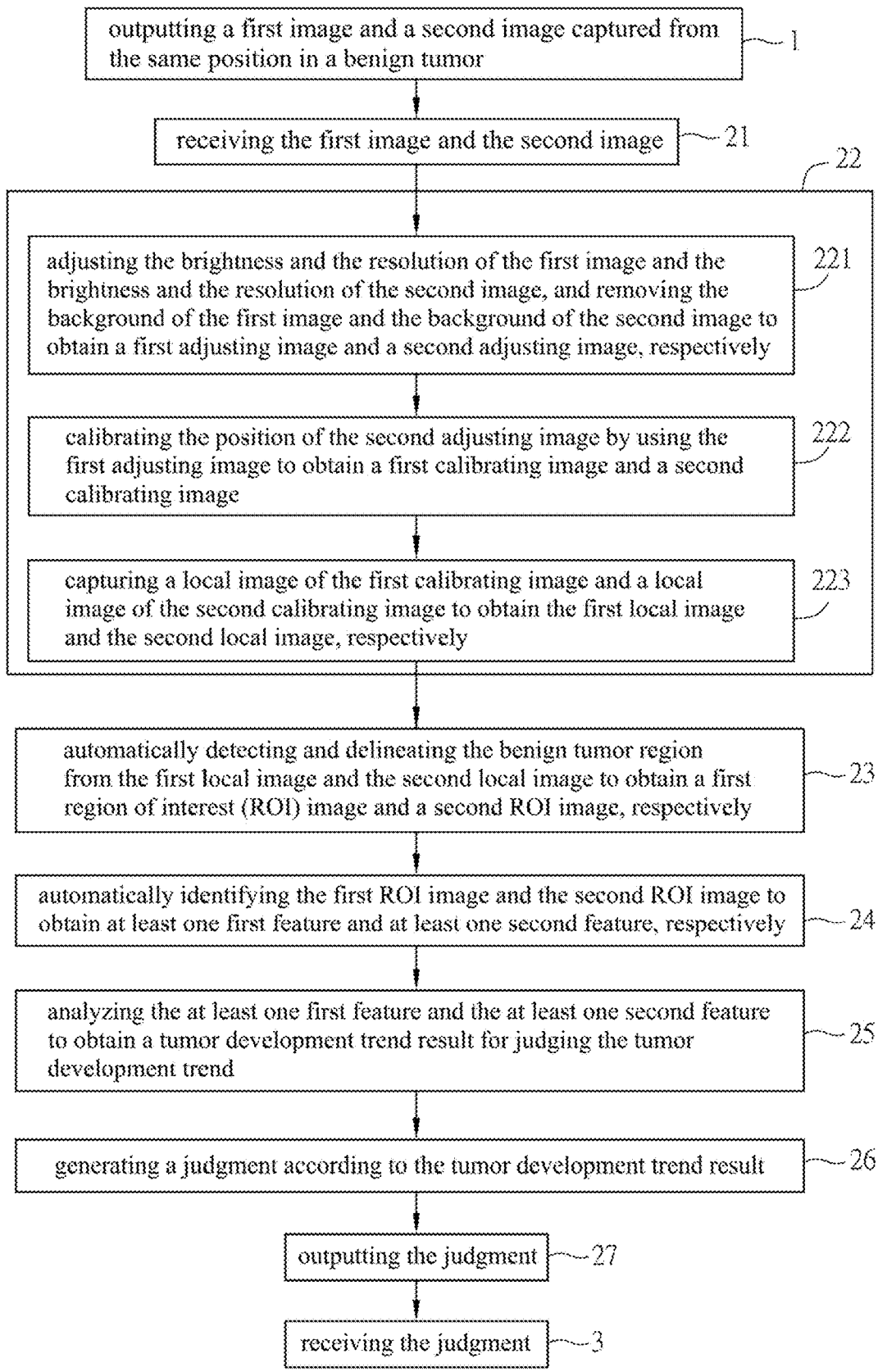
FIG. 3 is a flow chart of assessing processes of the benign tumor development trend assessment system of this disclosure.

Please refer to FIGS. 3, 1A, 1B and 4A to 4E, simultaneously. These figures illustrate the operation mode of the benign tumor development trend assessment system 100 of this invention. FIG. 3 is a flow chart of assessing processes of the benign tumor development trend assessment system of this disclosure. As shown in the figures, first of all, the image outputting device 1 outputs a first image I11 and a second image I21 captured from the same position in a benign tumor to the server computing device 2. Next, the server computing device 2 receives the first image I11 and the second image I21 outputted by the image outputting device 1 through the image receiving module 21. The server computing device 2 pre-processes the first image I11 and the second image I21 through the image pre-processing module 22 to obtain a first local image I14 and a second local image I24, respectively. Wherein, the image pre-processing comprises: adjusting the brightness and the resolution of the first image I11 and the brightness and the resolution of the second image I21, and removing the background of the first image I11 and the background of the second image I21 through the image adjusting unit 221 to obtain a first adjusting image I12 and a second adjusting image I22, respectively; calibrating the position of the second adjusting image I22 by using the first adjusting image I12 through the image calibrating unit 222 to obtain a first calibrating image I13 and a second calibrating image I23; and capturing a local image of the first calibrating image I13 and a local image of the second calibrating image I23 through the local image capturing unit 223 to obtain the first local image I14 and the second local image I24, respectively. Next, the server computing device 2 automatically detects and delineates a tumor region from the first local image I14 and the second local image I24 through the target extracting module 23 to obtain a first ROI image I15 and a second ROI image I25, respectively. Then, the server computing device 2 automatically identifies the first ROI image I15 and the second ROI image I25 through the feature extracting module 24 to obtain at least one first feature and at least one second feature, respectively. Next, the server computing device 2 analyzes the at least one first feature and the at least one second feature through the trend analyzing module 25 to obtain a tumor development trend result. Then, the server computing device 2 generates a judgment according to the tumor development trend result through the judging module 26 and outputs the judgment through the judgment outputting module 27 to the user computing device 3. Finally, the user computing device 3 receives the judgment outputted by the server computing device 2. Briefly, the image outputting device 1 outputs a first image I11 and a second image I21 captured from the same position in a benign tumor to the server computing device 2; the server computing device 2 automatically processed the first image I11 and the second image I21 to obtain the judgment; and then the judgment is outputted from the server computing device 2 to the user computing device 3. Herein, the image outputting device 1 may be, for example but not limited to, universal serial bus (USB), compact disk (CD), disc, computing device or MRI device which can store and output the images. The examples of the server computing device 2 and the user computing device 3 are described above, and will be omitted here.

Figure 7:
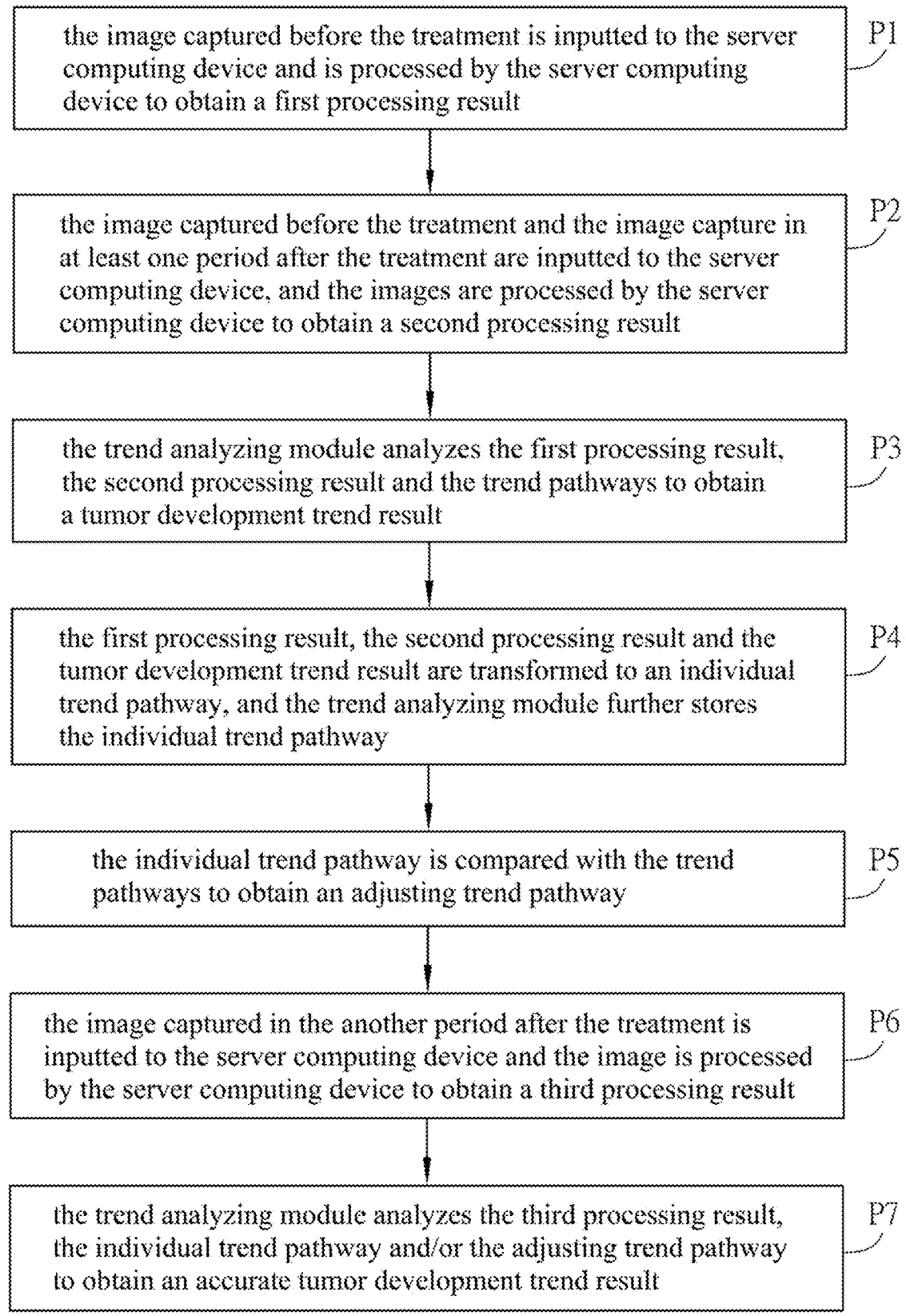
FIG. 7 is a flow chart of the method for enhancing an accuracy of a benign tumor development trend assessment system of this disclosure.

Please refer to FIGS. 1A and 7, simultaneously. FIG. 7 is a flow chart of the method for enhancing an accuracy of a benign tumor development trend assessment system of this disclosure. In this embodiment, a method for enhancing an accuracy of the above-mentioned benign tumor development trend assessment system is provided. This method is applied in the said benign tumor development trend assessment system for enhancing the accuracy of the benign tumor development trend assessment system.

As shown in FIG. 1A, the said benign tumor development trend assessment system 100 comprises the said image outputting device 1 and the said server computing device 2. The said server computing device 2 comprises the said trend analyzing module 25. The said trend analyzing module 25 stores a plurality of trend pathways. The said trend pathways are obtained by the said trend analyzing module 25 through analyzing a plurality of reference images. The said image outputting device 1 outputs an image captured from a benign tumor of a patient before a treatment and outputs an image captured from the benign tumor of the patient in at least one period after the treatment. In this embodiment, at least one image is captured from one patient before and after the treatment. In other words, the images are captured from the same patient before and after the treatment. In this embodiment, the images can be 2D images and 3D images. Preferably, the images can be 2D images. Preferably, the images can be 3D images. Preferably, the images can be 2D images and 3D images.

Figure 8:
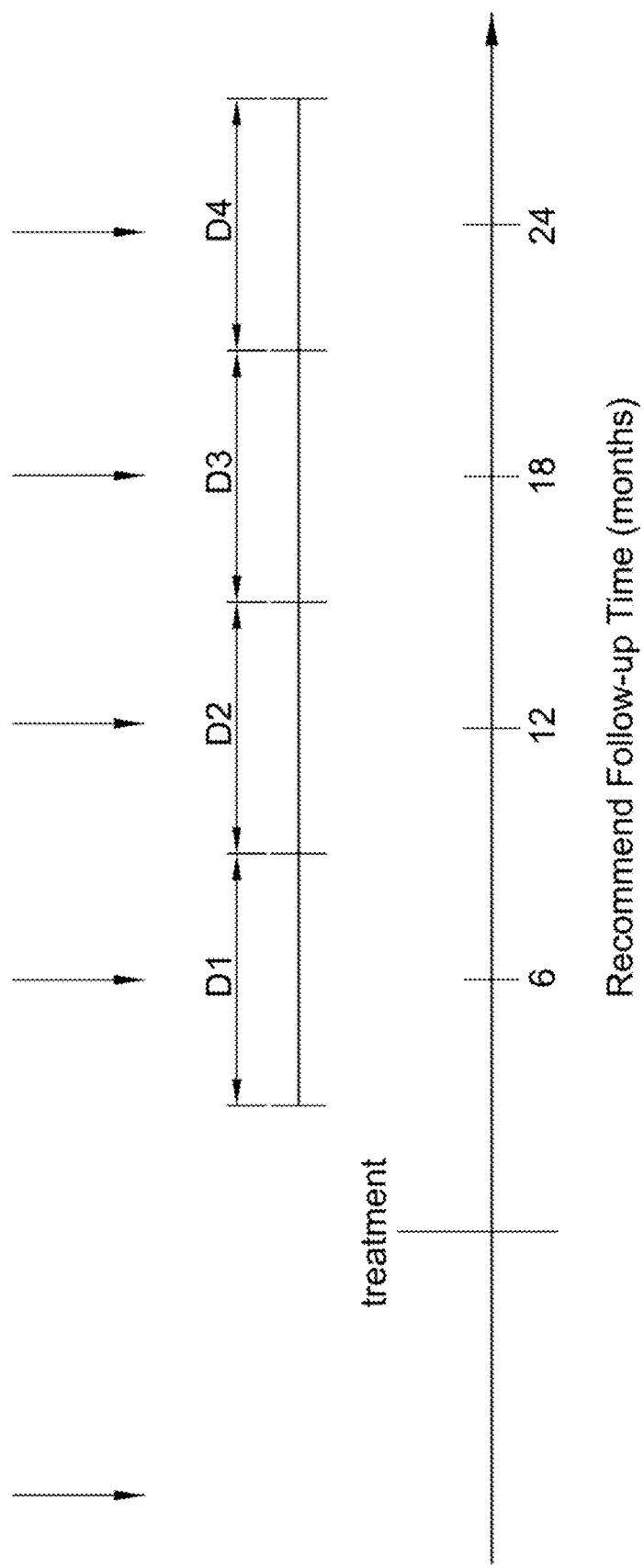
FIG. 8 is a schematic view of a preferred embodiment that showing the relationship between the period after the treatment and the recommend follow-up time point of this disclosure.

Please refer to FIG. 8, FIG. 8 is a schematic view of a preferred embodiment that showing the relationship between the period after the treatment and the recommend follow-up time point of this disclosure. The at least one period after the treatment is a plurality of periods, and at least one of the periods is partially overlapped with a recommend follow-up time point. For example, as shown in FIG. 8, there are 4 periods D1, D2, D3, D4 after the treatment and the recommend follow-up time point is 6 months after the treatment, 12 months after the treatment, 18 months after the treatment, or 24 months after the treatment. The period D1 is partially overlapped with a recommend follow-up time point (6 months after the treatment). The period D2 is partially overlapped with a recommend follow-up time point (12 months after the treatment). The period D3 is partially overlapped with a recommend follow-up time point (18 months after the treatment). The period D4 is partially overlapped with a recommend follow-up time point (24 months after the treatment). And the duration of the periods D1, D2, D3, D4 is 1 month, 2 months, 3 months, 4 months, 5 months, or 6 months. The arrows of FIG. 8 refer to the time point when the images are captured. The arrow at the left side of the treatment refers to the time point is before the treatment. The arrows above the periods D1, D2, D3, D4 refer to the time point are after the treatment. The time points when the image is captured can be variable in these periods D1, D2, D3, D4.

In this embodiment, the method comprises a first processing procedure P1, a second processing procedure P2, a trend analyzing procedure P3 and a storing procedure P4.

In the first processing procedure P1, the image captured before the treatment is inputted to the server computing device 2 and is processed by the server computing device 2 to obtain a first processing result. The image captured before the treatment is, for example but not limited to, T1-weighted (T1 W) image, T2-weighted (T2 W) image, or T1-weighted gadolinium contrast enhanced (T1 W+C) image. The image captured before the treatment is processed by for example but not limited to the image receiving module 21, the image pre-processing module 22, the target extracting module 23, the feature extracting module 24 and the trend analyzing module 25 of the server computing device 2 to obtain the first processing result. The procedures that processed by the image receiving module 21, the image pre-processing module 22, the target extracting module 23, the feature extracting module 24 and the trend analyzing module 25 are described above and will be omitted here.

In the second processing procedure P2, the image captured before the treatment and the image capture in at least one period after the treatment are inputted to the server computing device 2, and the images are processed by the server computing device 2 to obtain a second processing result. The image captured after the treatment is, for example but not limited to, T1-weighted (T1 W) image, T2-weighted (T2 W) image, or T1-weighted gadolinium contrast enhanced (T1 W+C) image. The images captured before and after the treatment are inputted to the server computing device 2, simultaneously. And then, the images are processed by for example but not limited to the image receiving module 21, the image pre-processing module 22, the target extracting module 23, the feature extracting module 24 and the trend analyzing module 25 of the server computing device 2 to obtain the second processing result. The procedures that processed by the image receiving module 21, the image pre-processing module 22, the target extracting module 23, the feature extracting module 24 and the trend analyzing module 25 are described above and will be omitted here.

In the trend analyzing procedure P3, the trend analyzing module 25 analyzes the first processing result, the second processing result and the trend pathways to obtain a tumor development trend result. The tumor development trend result may be a prediction that the benign tumor has non-response to the radiation treatment or a prediction that the benign tumor has a response (with or without pseudo-progression) to the radiation treatment.

In the storing procedure P4, the first processing result, the second processing result and the tumor development trend result are transformed to an individual trend pathway, and the trend analyzing module 25 further stores the individual trend pathway. The individual trend pathway can be analysis by the trend analyzing module 25 when the same patient goes to the hospital and takes new images after the treatment. Meanwhile, the individual trend pathway can increase the data in the database or in the trend analyzing module 25.

As shown in FIG. 7, in some embodiments, the method can further comprises an adjusting procedure P5. In the adjusting procedure P5, the individual trend pathway is compared with the trend pathways to obtain an adjusting trend pathway. The adjusting trend pathway can enhance the accuracy of the benign tumor development trend assessment system 100.

Please refer to FIGS. 7-8. In some embodiments, the image outputting device 1 may further outputs an image captured from the benign tumor of the patient in another period after the treatment. In more detailed, the images of a patient are captured before and after the treatment. The image is captured in period D1 after the treatment when the patient goes to the hospital for the first time after the treatment. The first processing procedure P1, the second processing procedure P2, the trend analyzing procedure P3, the storing procedure P4 and the adjusting procedure P5 are processed by the server computing device 2 according to the images captured before the treatment and in the period D1 after the treatment. When the patient goes to the hospital for the second, the third or the fourth time (i.e. in the period D2, D3, or D4) after the treatment and takes the images. These images are the images which are captured in another period (i.e. in the period D2, D3, or D4) after the treatment.

In some embodiments, the method may further comprises a third processing procedure P6 and an accurate trend analyzing procedure P7. In the third processing procedure P6, the image captured in the another period after the treatment is inputted to the server computing device 2 and the image is processed by the server computing device 2 to obtain a third processing result. In the accurate trend analyzing procedure P7, the trend analyzing module 25 analyzes the third processing result, the individual trend pathway and/or the adjusting trend pathway to obtain an accurate tumor development trend result. Preferably, the trend analyzing module 25 analyzes the third processing result and the individual trend pathway to obtain an accurate tumor development trend result of the patient. Preferably, the trend analyzing module 25 analyzes the third processing result and the adjusting trend pathway to obtain an accurate tumor development trend result of the patient. Preferably, the trend analyzing module 25 analyzes the third processing result, the individual trend pathway and the adjusting trend pathway to obtain an accurate tumor development trend result of the patient.

In the previous embodiments, the images of the benign tumor are automatically detected and delineated by the benign tumor development trend assessment system 100 to obtain volumes of the images of the benign tumor in the first processing procedure, the second processing procedure, or the third processing procedure, respectively. In more detailed, a patient who has benign tumor goes to the hospital and takes at least one image before the treatment. Then, the same patient who has benign tumor goes to the hospital and takes at least one image in at least one periods after the treatment. These images are inputted to the server computing device 2 of the tumor development trend assessment system 100. And then volumes of the images of the benign tumor of the patient and the tumor development trend result or the accurate tumor development trend result are automatically obtained at the same time by the tumor development trend assessment system 100. Meanwhile, these data of the patient were integrated into the tumor development trend assessment system 100, so as to enhance the accuracy of the tumor development trend assessment system 100. When a new patient goes to the hospital, the new images of the new patient are analyzed with the said trend pathways, the said individual trend pathway and/or the said adjusting trend pathway by the tumor development trend assessment system 100 to obtain a more accurate tumor development trend result of the new patient.

EXAMPLES

Reference Images Database

Reference images were captured from the patients with VS who are treated at Taipei Veteran General Hospital in Taiwan from 1993 to 2019. Overall 336 patients with no previous craniotomy for tumor removal and a minimum of 24-month follow-up period (with a median follow-up of 65.1 months) after radiosurgery were finally included in this study. The informed consent to participate which are approved by the Institutional Review Board (IRB) of the hospital are signed by the patients of this study. The reference images are MRI images, including T1 W+C images, T2 W images, and T1 W images, and were obtained from each patients by using a 1.5-T MR scanner (Signa Horizon LX2, GE Medical Systems) before the radiation treatment, after the radiation treatment and at follow-up. Herein, the radiation treatment is GKRS. Then, the tumor volumes were longitudinally measured (in $cm^3$) by experienced neuroradiologists based on MRI images obtained before the radiation treatment, after the radiation treatment and at follow-up. According to the response of VS to the radiation treatment (GKRS), the patients were further categorized into three groups, including the tumor has a response without pseudo-progression (130 patients), tumor has a response with pseudo-progression (135 patients), and tumor has non-response (71 patients) groups. The clinical characteristics of the patients of these three groups in the study cohort are listed in Table 1.

TABLE 1

Clinical characteristics of 336 patients with VS

| | Tumor has a response | | |
|---|---|---|---|
| Tumor response after GKRS | Without pseudo-progression | With pseudo-progression | Tumor has Non-response |
| Patient number | 130 | 135 | 71 |
| Patient age (years) | 54.0 ± 13.5 | 50.1 ± 13.6 | 50.7 ± 13.7 |
| Female: male ratio | 71:59 | 76:59 | 50:21 |
| Gross tumor volume ($cm^3$) | 4.26 ± 3.62 (0.16-14.35) | 3.39 ± 3.83 (0.14-17.10) | 2.41 ± 3.02 (0.10-16.70) |
| Prescribed dose (Gy) | 12.1 ± 0.5 | 12.2 ± 0.6 | 12.1 ± 0.6 |
| Maximum dose (Gy) | 21.2 ± 0.9 | 21.1 ± 1.2 | 20.8 ± 1.4 |
| Follow-up (months) | 72.7 ± 37.2 | 77.9 ± 39.6 | 68.2 ± 39.1 |
| Six-month volume change ratio (%) | −13.1 ± 17.4 | 37.2 ± 32.6 | 29.4 ± 35.1 |
| Twelve-month volume change ratio (%) | −32.8 ± 24.6 | 5.3 ± 28.4 | 26.2 ± 40.7 |
| Eighteen-month volume change ratio (%) | −39.5 ± 25.4 | −2.5 ± 37.9 | 27.9 ± 39.3 |
| Two-year Volume change ratio (%) | −53.2 ± 22.5 | −21.2 ± 42.7 | 33.5 ± 56.5 |
| Final volume change ratio (%) | −66.0 ± 20.6 | −48.3 ± 22.4 | 48.9 ± 93.7 |

As shown in Table 1, Table 1 lists the clinical characteristics of the 336 patients with VS. There were no significant differences in the patient age, gender, prescribed dose, and maximum dose among three response groups. The gross tumor volume in the tumor has non-response group was significantly smaller than that in the tumor has a response without pseudo-progression group (p<0.001). Regarding the longitudinal changes of tumor volume after GKRS, the group of tumor has a response without pseudo-progression showed a gradual reduction of tumor volume from −13.1±17.4% to −66.0±20.6% between the six-month and final follow-up. The group of tumor has a response with pseudo-progression exhibited a different pattern, that a significant increment of tumor volume (37.2±32.6%) at six-month follow-up followed by a gradual reduction to −48.3±22.4% until the final follow-up. For the tumor has non-response group, the tumor volume increased from 29.4±35.1% at six-month follow-up to 48.9 f 93.7% at the final follow-up.

Image Pre-Processing:

Several pre-processing steps on the MRI images of 366 patients were applied to reduce the discrepancy of imaging parameters and to improve the reliability of radiomics analysis. The adjustment of image resolution was first performed to resample all voxel size to 0.50×0.50×3.00 $mm^3$ without gaps between consecutive slices for each MR modalities. The T2 W images and T1 W images were then registered to the T1 W+C images (captured from the same patient) using a six-parameter rigid body transformation and mutual information algorithm. Following, the local images (comprise the image of the benign tumor and the image of the tissue near the benign tumor) of the MRI images were captured and then the tumor region were delineated to obtain the ROI images.

Trend Pathways Establishment:

Next, the ROI images were analyzed based on radiomics to extract grayscale features and texture features. Then, the features were compared by statistical analysis to find out the features exhibited significant differences between these three groups, so as to establish the trend pathways.

The features exhibited significant differences between the "tumor has a response to the radiation treatment" group and the "tumor has non-response to the radiation treatment" group:

Three features exhibited significant differences (p<3.65×$10^5$) between the "tumor has a response to the radiation treatment" and "tumor has non-response to the radiation treatment" groups (hereinafter "tumor has a response" and "tumor has non-response") and listed in Table 2. The three features were grayscale features and texture features obtained from T2 W images and T1 W+C images. Grayscale features were standard deviation and root mean square which were obtained from T2 W images by using histogram filter. Texture feature was the mean of LBP which was obtained from T1 W+C images by using LBP filter. These three features indicated the tumor status was cystic tissue or loose tissue.

TABLE 2

| Image name | Radiomics type and wavelet filtering | Feature name | Tumor has a response | Tumor has non-response |
|---|---|---|---|---|
| T1W + C | Texture-LBP (LLH*) | Mean of LBP | 0.11 ± 0.95 | −0.44 ± 0.98 |

TABLE 2-continued

| Image name | Radiomics type and wavelet filtering | Feature name | Tumor has a response | Tumor has non-response |
|---|---|---|---|---|
| T2W | Histogram | standard deviation | 0.06 ± 0.94 | −0.45 ± 0.59 |
| T2W | Histogram | root mean square | 0.09 ± 0.98 | −0.43 ± 0.68 |

*LLH was wavelet filter. L represents a low-pass filter, and H represents a high-pass filter. The combination of three letters of L and H stands for the filter type applied to the three image axis (X, Y and Z) by order. In other words, low-pass filter was applied to X and Y axis of the images, and high-pass filter was applied to Z axis of the images.

The features exhibited significant differences between the "tumor has a response to the radiation treatment without pseudo-progression" group and the "tumor has a response to the radiation treatment with pseudo-progression" group:

Three features exhibited significant differences ($p<3.65\times 10^5$) between the "tumor has a response to the radiation treatment without pseudo-progression" and "tumor has a response to the radiation treatment with pseudo-progression" groups (hereinafter "tumor has a response without pseudo-progression" and "tumor has a response with pseudo-progression") and listed in Table 3. These three features were grayscale features and texture features obtained from T2 W images and T1 W+C images. Texture feature was the LRLGLE which obtained from T1 W+C images by using GLRLM filter. And one of grayscale feature was skewness which obtained from T1 W+C images by using histogram filter. Another one of grayscale feature was standard deviation which obtained from T2 W images by using histogram filter. It is to be noted that, the feature of standard deviation which obtained from T2 W images can be used to distinguish the tumor has a response to the radiation treatment and the tumor has non-response to the radiation treatment. When the assessment is that the tumor has a response to the radiation treatment, standard deviation obtained from T2 W images can further be used to distinguish the tumor has a response with or without pseudo-progression.

TABLE 3

| Image name | Radiomics type and wavelet filtering | Feature name | Tumor has a response Without pseudo-progression | Tumor has a response With pseudo-progression |
|---|---|---|---|---|
| T1W + C | Texture-GLRLM | LRLGLE | −0.32 ± 0.85 | 0.20 ± 0.80 |
| T1W + C | Histogram | skewness | 0.24 ± 0.96 | −0.29 ± 0.82 |
| T2W | Histogram | standard deviation | 0.23 ± 0.97 | −0.30 ± 0.78 |

The above-mentioned features obtained from MRI images of 336 patients were analyzed respectively. The features in Table 2 were used for the first assessment, and the features in Table 3 were used for the second assessment. Wherein, the first assessment could use to establish the trend pathways which could distinguish "the tumor has a response to the radiation treatment" and "the tumor has non-response to the radiation treatment". The second assessment could use to establish the trend pathways which could distinguish "the tumor has a response to the radiation treatment with pseudo-progression" and "the tumor has a response to the radiation treatment without pseudo-progression".

Figure 5A:
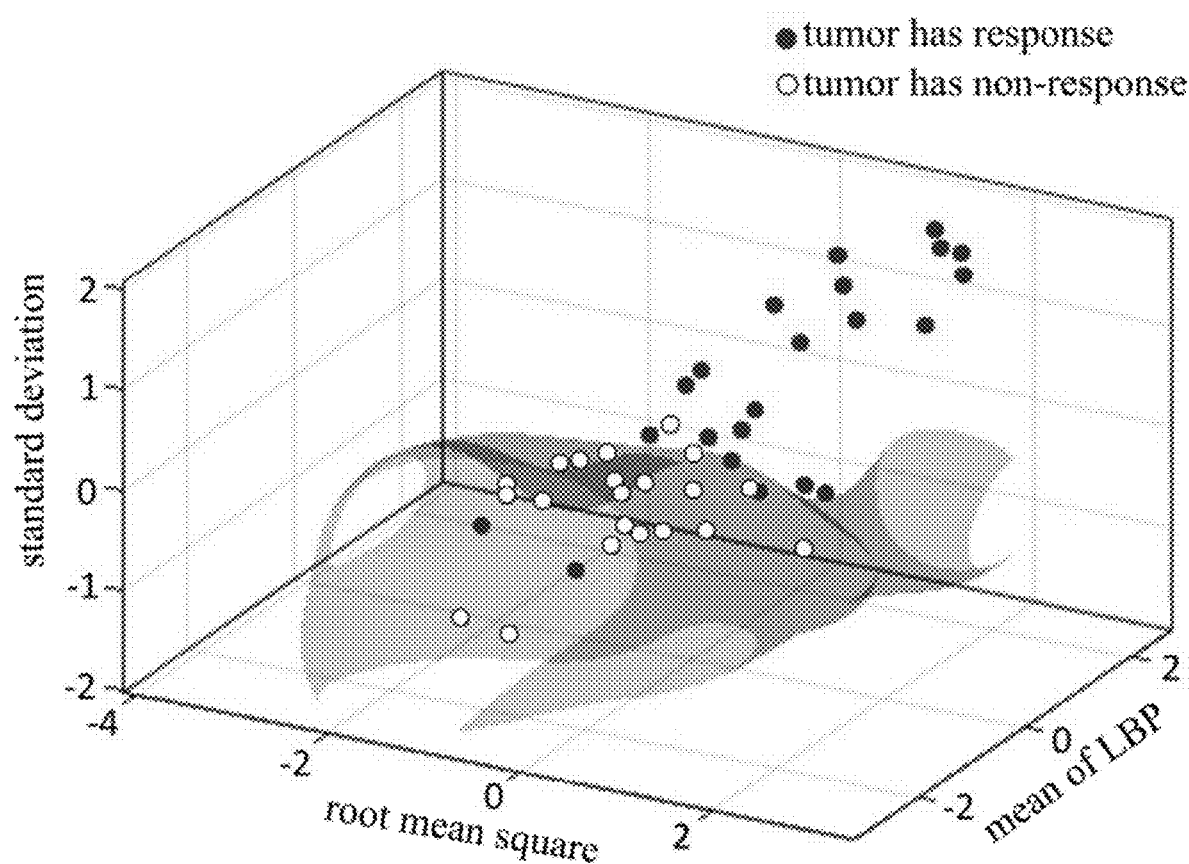
FIGS. 5A-5C are schematic views showing that the benign tumor development trend assessment system of this disclosure obtains the tumor development trend result by analyzing tumor features, wherein the tumor development trend result is that "the benign tumor has non-response to the radiation treatment" or "the benign tumor has a response to the radiation treatment".
Figure 5B:
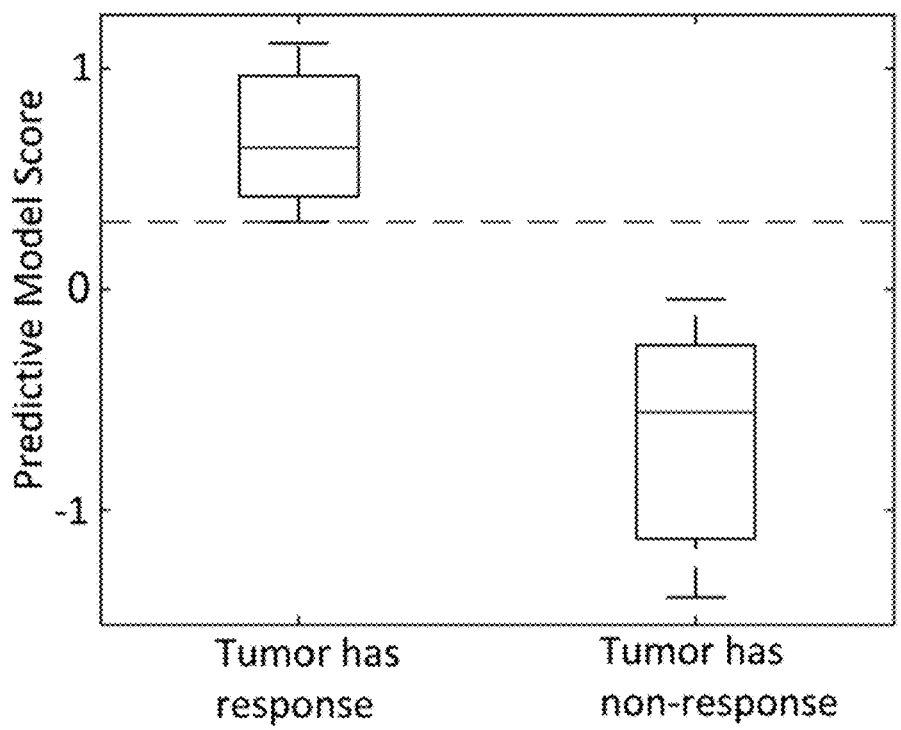
Figure 5C:
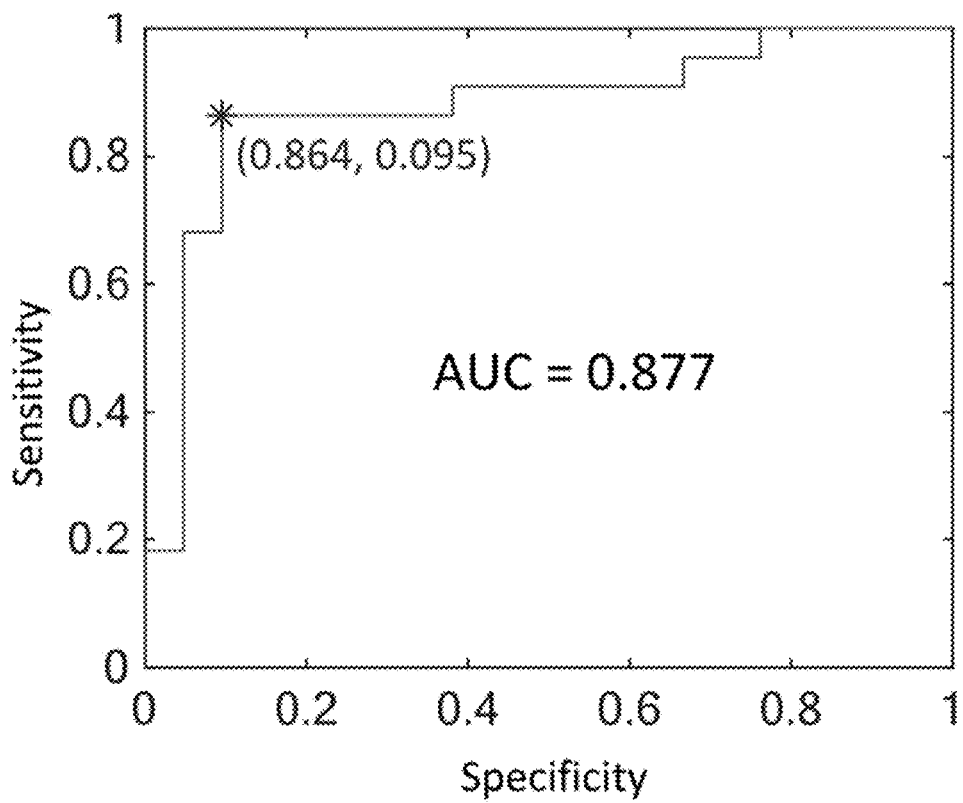

For Predicting/Judging the Tumor has a Response to the Radiation Treatment or the Tumor has Non-Response to the Radiation Treatment:

Please refer to FIGS. 5A to 5C for illustrating the trend pathways which were established in the first assessment. FIGS. 5A-5C are schematic views showing that the benign tumor development trend assessment system of this disclosure obtains the tumor development trend result by analyzing tumor features, wherein the tumor development trend result is that "the benign tumor has non-response to the radiation treatment" or "the benign tumor has a response to the radiation treatment". As shown in FIG. 5A, FIG. 5A shows the three-dimensional scatter plots of tumor features of a plurality of reference images. The tumor has non-response group represented as hollow circular points, and the tumor has a response group represented as black circular points. The three-dimensional scatter plots of the features of mean of LBP, standard deviation and root mean square of these two groups could be separated by a gray surface to establish different trend pathways. When three features were obtained from a new image according to the above-mentioned methods, the three-dimensional scatter plots of features of the new image were analyzed and find out the location of the new points would be near the black circular points or the hollow circular points, so as to judge the tumor of new tumor image will have non-response to the radiation treatment or the tumor of new tumor image will have a response to the radiation treatment. As shown in FIG. 5B, FIG. 5B shows the predictive model scores transferred from the tumor features of FIG. 5A. The predictive model scores of these two groups could be separated by the dash line. When three features were obtained from a new image according to the above-mentioned methods, the predictive model scores of the new image would be transferred from the three-dimensional scatter plots of the features of the new image. The tumor of new tumor image will have non-response to the radiation treatment or the tumor of new tumor image will have a response to the radiation treatment could be judged by analyzing the predictive model score is above the dash line or under the dash line. As shown in FIG. 5C, FIG. 5C shows the resultant receiver operating characteristic curves for assessing "the benign tumor has non-response to the radiation treatment" or "the benign tumor has a response to the radiation treatment". When the above-mentioned three features were used to predict/judge the tumor has a response to the radiation treatment or the tumor has non-response to the radiation treatment, the resultant receiver operating characteristic curves can achieve AUC (area under the curve) =0.877 (sensitivity=86.4%, specificity=90.5%, and accuracy=88.4%). The above-mentioned three features could use, for example but not limited to, SVM, manual, or gap analysis to obtained the results of FIGS. 5A to 5C.

Figure 6A:
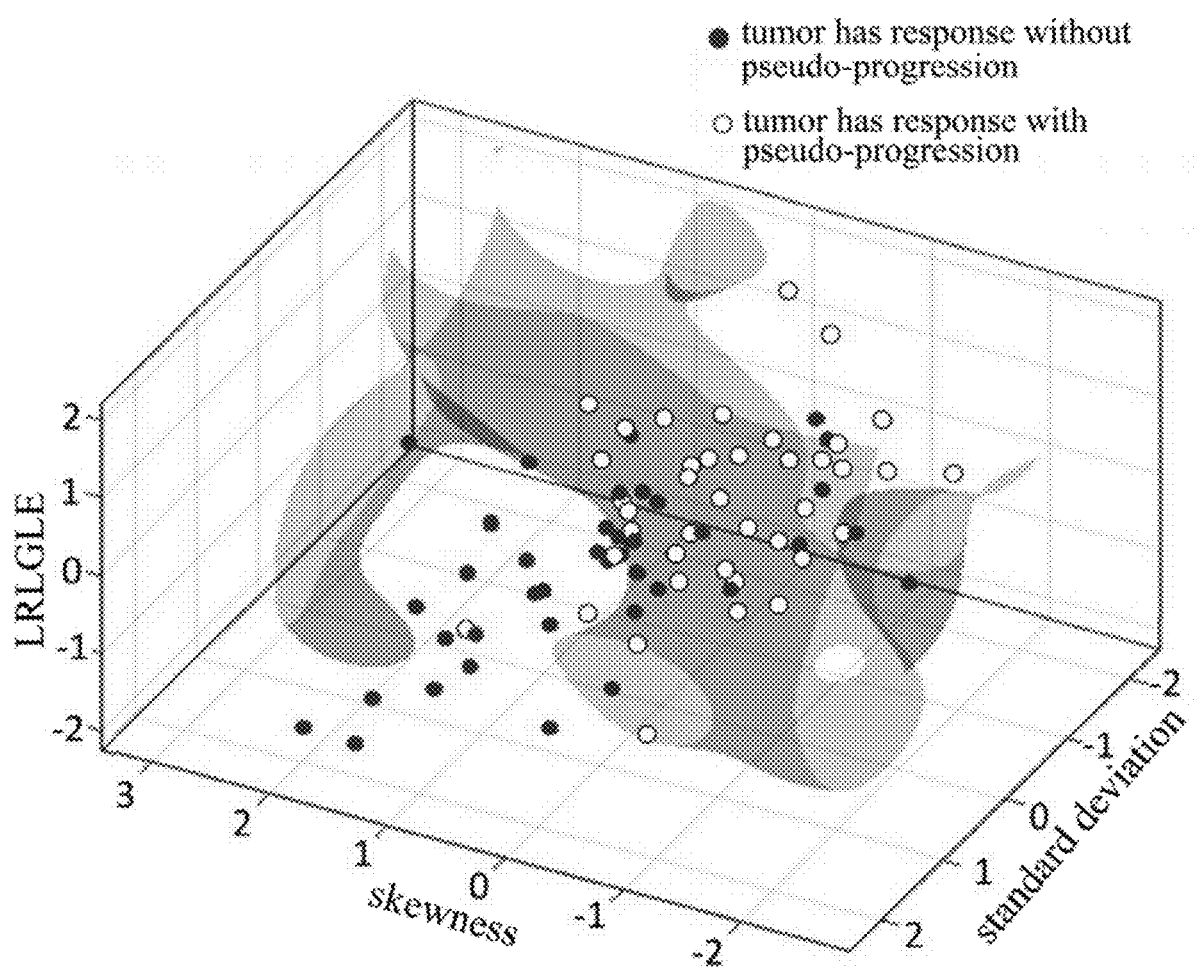
FIGS. 6A-6C are schematic views showing that the benign tumor development trend assessment system of this disclosure obtains the tumor development trend result by analyzing tumor features, wherein the tumor development trend result is that "the benign tumor has a response to the radiation treatment with pseudo-progression" or "the benign tumor has a response to the radiation treatment without pseudo-progression".
Figure 6B:
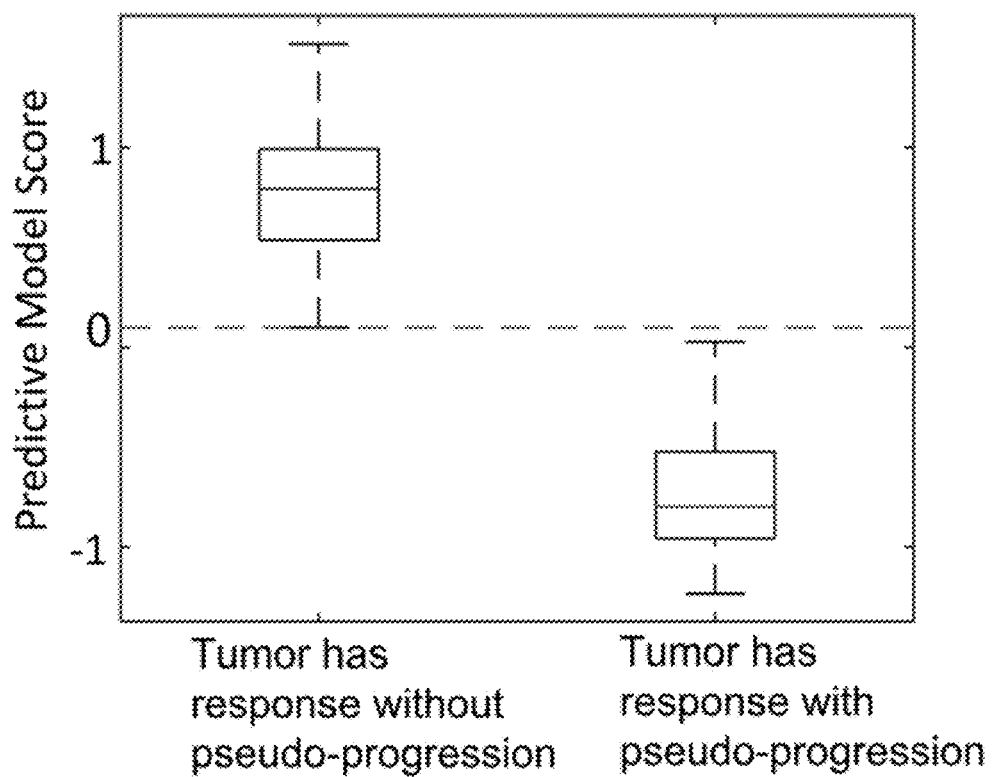
Figure 6C:
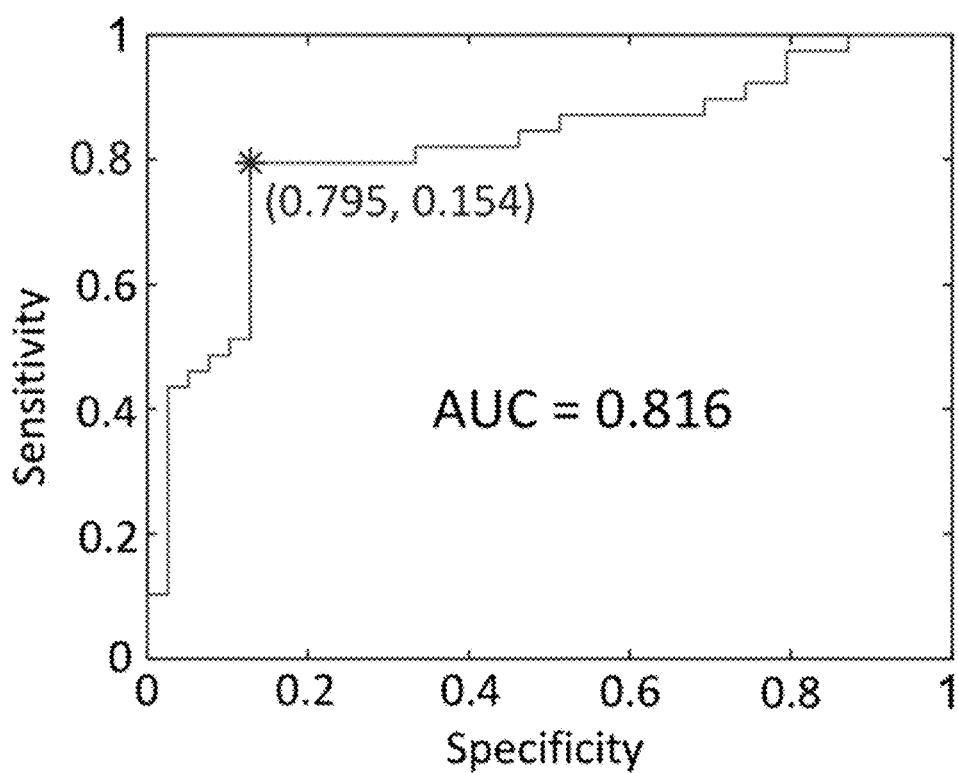

When the Judgment is "the Benign Tumor has a Response to the Radiation Treatment", Further Predicting/Judging "the Tumor has a Response to the Radiation Treatment with Pseudo-Progression" or "the Tumor has a Response to the Radiation Treatment without Pseudo-Progression":

Please refer to FIGS. 6A to 6C for illustrating the trend pathways which were established in the second assessment. FIGS. 6A-6C are schematic views showing that the benign tumor development trend assessment system of this disclosure obtains the tumor development trend result by analyzing tumor features, wherein the tumor development trend result is that "the benign tumor has a response to the radiation treatment with pseudo-progression" or "the benign tumor has a response to the radiation treatment without pseudo-progression". As shown in FIG. 6A, FIG. 6A shows the three-dimensional scatter plots of tumor features of a plurality of reference images. The tumor has a response with pseudo-progression group represented as hollow circular points, and the tumor has a response without pseudo-progression group represented as black circular points. The three-dimensional scatter plots of the features of LRLGLE, skewness and standard deviation of these two groups could be separated by a gray surface to establish different trend pathways. When these three features were obtained from a new image according to the above-mentioned methods, the three-dimensional scatter plots of the features of the new image were analyzed and find out the location of the new points would be near the black circular points or the hollow circular points, so as to judge the tumor of new tumor image will have a response with pseudo-progression or the tumor of new tumor image will have a response without pseudo-progression. As shown in FIG. 6B, FIG. 6B shows the predictive model scores transferred from the tumor features of FIG. 6A. The predictive model scores of these two groups could be separated by the dash line. When these three features were obtained from a new image according to the above-mentioned methods, the predictive model scores of the new image would be transferred from the three-dimensional scatter plots of the features of the new image. The tumor of new tumor image will have a response with pseudo-progression or the tumor of new tumor image will have a response without pseudo-progression could be judged by analyzing the predictive model score is above the dash line or under the dash line. As shown in FIG. 6C, FIG. 6C shows the resultant receiver operating characteristic curves for assessing "the benign tumor has a response to the radiation treatment with pseudo-progression" or "the benign tumor has a response to the radiation treatment without pseudo-progression". When the above-mentioned three features were used to predict/judge the tumor has a response to the radiation treatment with pseudo-progression or the tumor has a response to the radiation treatment without pseudo-progression, the resultant receiver operating characteristic curves can achieve AUC=0.816 (sensitivity=79.5%, specificity=84.6%, and accuracy=82.1%). The above-mentioned three features could use, for example but not limited to, SVM, manual, or gap analysis to obtained the results of FIGS. 6A-6C.

Individual Trend Pathways Establishment:

When a new patient goes to the hospital, a new image of the new patient which is captured before the treatment is processed and analyzed by the above-mentioned procedures, so as to obtain the first processing result. The first processing result is that "the tumor has non-response to the radiation treatment", "the tumor has a response to the radiation treatment with pseudo-progression" or "the tumor has a response to the radiation treatment without pseudo-progression". Therefore, the new patient and the health care professionals may discuss whether the treatment would be continued or not according to the first processing result (i.e. the tumor development trend result which is predicted before the treatment). After that, a new image of the new patient is captured in at least one period after the treatment. The images which are captured before and after the treatment were processed and analyzed by the above-mentioned procedures, so as to obtain the second processing result. Next, the first processing result and the second processing result are analyzed by the trend analyzing module to obtain a tumor development trend result after the treatment of the patient. After that, the first processing result, the second processing result and the tumor development trend results are transformed to an individual trend pathway of the new patient and be stored in the trend analyzing module 25.

Adjusting Trend Pathway Establishment:

The individual trend pathway of the new patient would be compared with the trend pathways of the reference images, and then an adjusting trend pathway would be obtained by the trend analyzing module.

Accurate Tumor Development Trend Result of the New Patient:

After the individual trend pathway and the adjusting trend pathway are established, a more accurate tumor development trend result of the new patient would be obtained by the benign tumor development trend assessment system 100. In more detailed, a new image of the new patient which is captured in any period after the treatment (the any period is different from the at least one period which is used to obtain the second processing result) is processed and analyzed by the above-mentioned procedures, so as to obtain the third processing result. The trend analyzing module analyzes the third processing result, the individual trend pathway and the adjusting trend pathway to obtain an accurate tumor development trend result of the new patient. Because the new image of the new patient which is captured in any period after the treatment is processed and analyzed according to the individual trend pathway of the new patient himself or herself and/or the adjusting trend pathway (which has been adjusted according to the individual trend pathway). Thus, the tumor development trend result of the new image of the new patient which is captured in any period after the treatment would be more accurate.

Figure 9A:
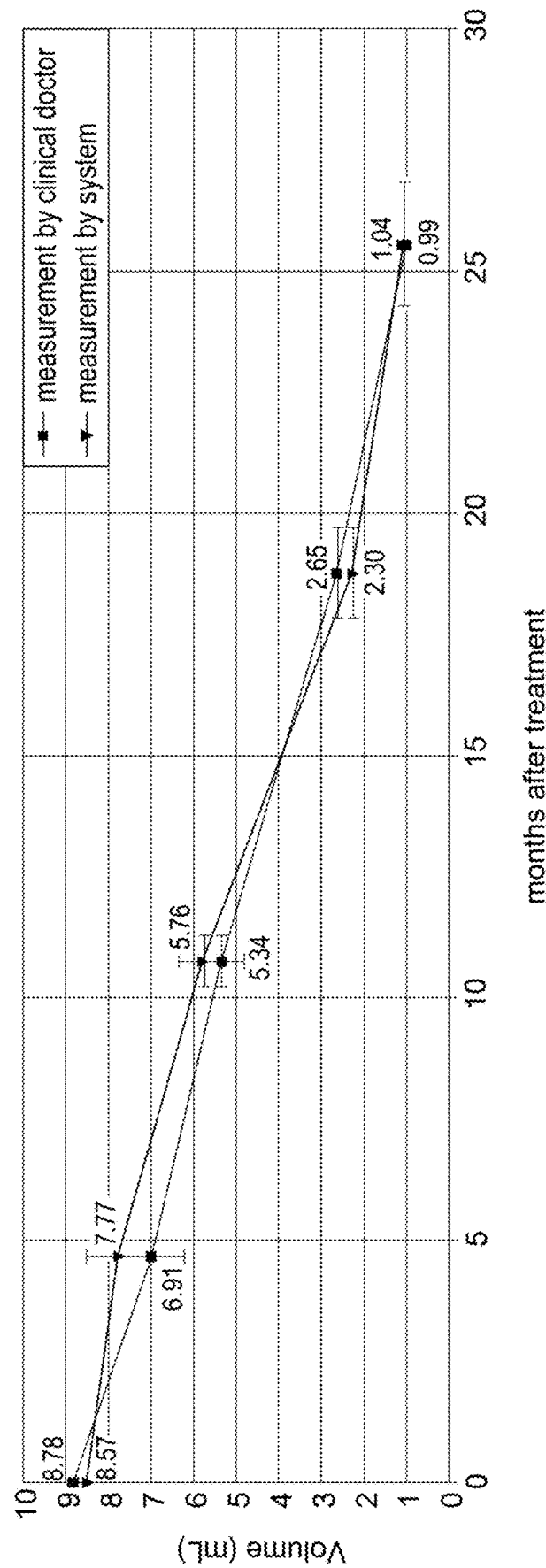
FIGS. 9A-9C are schematic views showing that the benign tumor volume after treatment which is measured by the benign tumor volume development trend assessment system of this disclosure or by the clinical doctor.
Figure 9B:
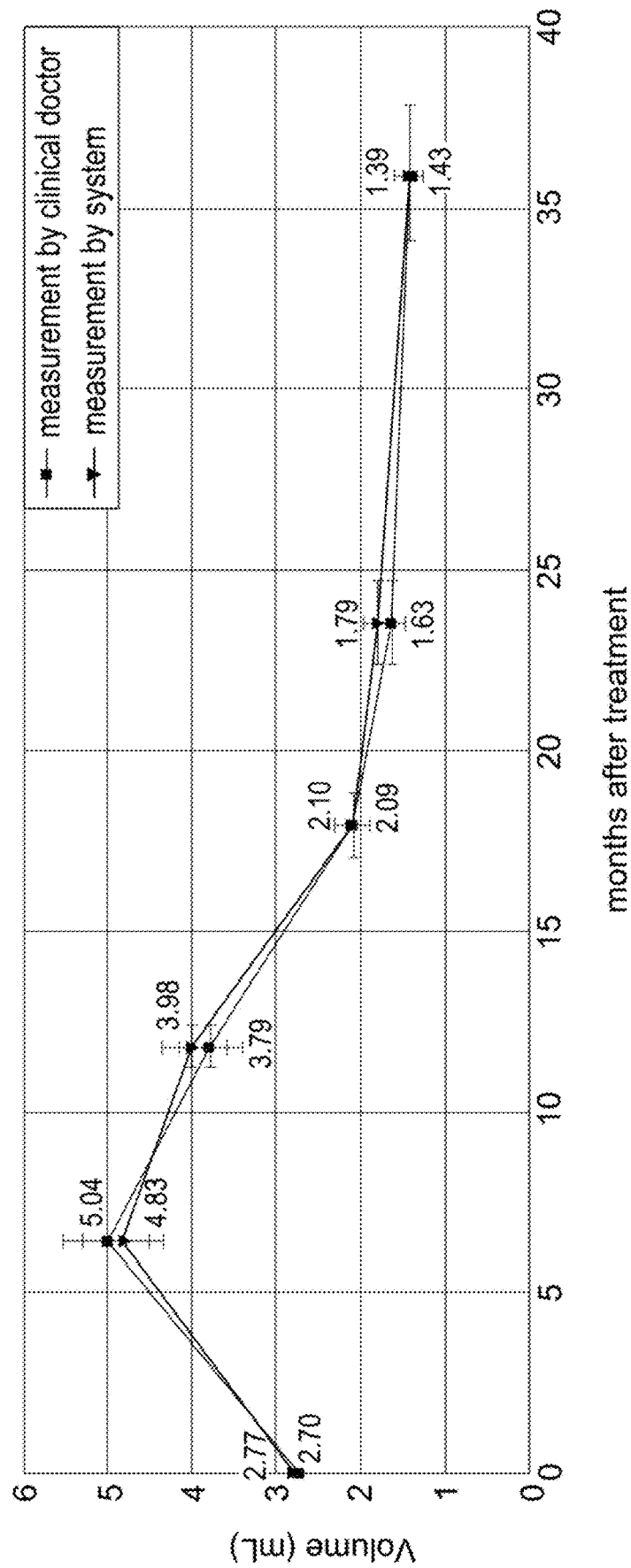
Figure 9C:
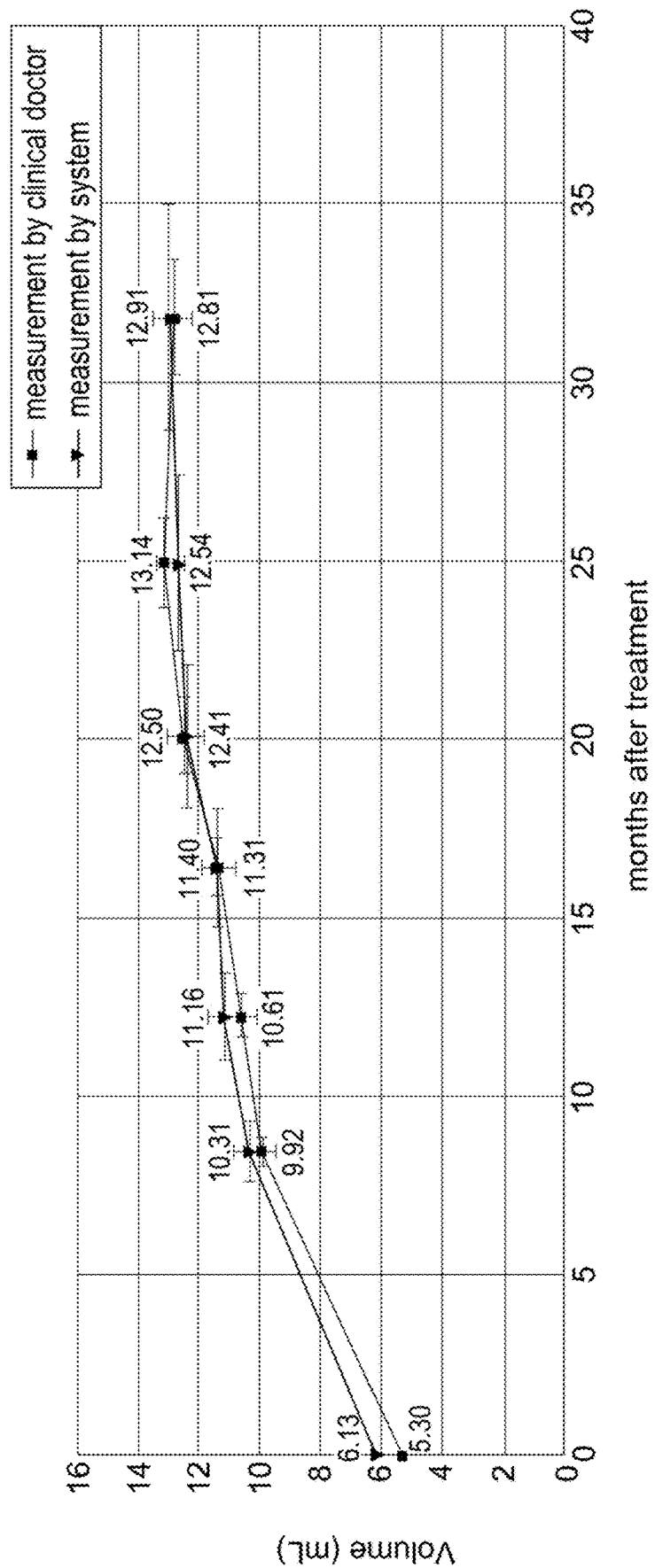

Volume Estimation:

All the images (including the reference images and any images of new patients) of the benign tumor are automatically detected and delineated by the benign tumor development trend assessment system 100 to obtain the volumes of the images of the benign tumor. And the volumes of the images which are delineated by the benign tumor development trend assessment system are compared with the volumes of the images which are delineated by a clinical doctor. Please refer to FIGS. 9A-9C, FIGS. 9A-9C are schematic views showing that the benign tumor volume after treatment which is measured by the benign tumor volume development trend assessment system of this disclosure or by the clinical doctor. FIG. 9A shows the result that the tumor volume of a patient which is decreased after the treatment (i.e. the benign tumor has a response to the radiation treatment without pseudo-progression). FIG. 9B shows the result that the tumor volume of a patient which is increased and then decreased after the treatment (i.e. the benign tumor has a response to the radiation treatment with pseudo-progression). FIG. 9C shows the result that the tumor volume of a patient which is increased after the treatment (i.e. the benign tumor has non-response to the radiation treatment). According to FIGS. 9A-9C, the difference between the volume measurements by the benign tumor development trend assessment system and the clinical doctor is less than 10%. Because the tumor regions have to be manually contoured by experienced doctors by repeatedly reviewing tumor images to measure the tumor volume, and it is nearly impossible to ask the same doctor to repeatedly reviewing tumor images and measure the tumor volume of the patient at any time after the treatment. Therefore, the images may be measured by different doctors at different time points when the patient goes to the hospital after the treatment. The volumes which are measured by different doctors may have variations. Thus, subjective annotations of the doctors are inevitable and the process of measuring the volume of the benign tumor is time consuming. Fortunately, the volumes obtained by the benign tumor development trend assessment system are remarkably accurate. Thus, the benign tumor development trend assessment system also provides an accurate and automatic method to measure the volumes of the images of the benign tumor.

As mentioned above, the tumor development trend assessment system of this invention can automatically assess the tumor development trend and the tumor volume according to the tumor images, and then the system provides the various advices to the health care professionals according to the assessment results. The benign tumor development trend assessment system can provide better treatment methods according to different patients to increase the efficacy of the treatments. In addition, the system also can be used to assess whether pseudo-progression would occur in the patient and let the patient know in advance. It is helpful to reduce the anxiety in patient and the psychological stress of the health care professionals. In addition, a method for enhancing the accuracy of the tumor development trend assessment system is also involved in this invention. Therefore, the accuracy of the tumor development trend assessment system is very high.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method for enhancing an accuracy of a benign tumor development trend assessment system, the benign tumor development trend assessment system comprising an image outputting device and a server computing device, the server computing device comprising a trend analyzing module, the trend analyzing module storing a plurality of trend pathways, the trend pathways being obtained by the trend analyzing module through analyzing a plurality of reference images, and the image outputting device outputting an image captured from a benign tumor of a patient before a treatment and outputting an image captured from the benign tumor of the patient in at least one period after the treatment, the image comprising a T1-weighted (T1W) MRI image, T2-weighted (T2W) MRI image or T1-weighted gadolinium contrast enhanced T1W+C) MRI image, the method comprising:

a first processing procedure, the image captured before the treatment is inputted to the server computing device and is processed by the server computing device to obtain a first processing result;

a second processing procedure, the image captured before the treatment and the image captured in at least one period after the treatment are inputted to the server computing device, and the images are processed by the server computing device to obtain a second processing result, wherein in the first processing procedure and the second processing procedure, a tumor region is automatically detected and delineated from the captured image by using U-Net neural network or 3D dual-pathway U-Net neural network, a grayscale feature is obtained from the captured image by using a histogram filter, a texture feature is obtained the captured image by using a gray-level run-length matrix (GLRLM) filter;

a trend analyzing procedure, the trend analyzing module analyzes the first processing result, the second processing result and the trend pathways through support vector machine (SVM), manual or gap analysis to obtain a tumor development trend result; and a storing procedure, the first processing result, the second processing result and the tumor development trend result are transformed to an individual trend pathway, and the trend analyzing module further stores the individual trend pathway.

2. The method according to claim 1, further comprising:
an adjusting procedure, the individual trend pathway is compared with the trend pathways to obtain an adjusting trend pathway.

3. The method according to claim 2, wherein the image outputting device further outputs an image captured from the benign tumor of the patient in another period after the treatment.

4. The method according to claim 3, further comprising:
a third processing procedure, the image captured in the another period after the treatment is inputted to the server computing device and the image is processed by the server computing device to obtain a third processing result; and an accurate trend analyzing procedure, the trend analyzing module analyzes the third processing result, the individual trend pathway and/or the adjusting trend pathway to obtain an accurate tumor development trend result.

5. The method according to claim 4, wherein the images of the benign tumor are automatically detected and delineated by the benign tumor development trend assessment system to obtain volumes of the images of the benign tumor and volume change ratios in the first processing procedure, the second processing procedure, or the third processing procedure, respectively.

6. The method according to claim 1, wherein the images are captured from one patient.

7. The method according to claim 1, wherein the images are 2D images and/or 3D images.

8. The method according to claim 1, wherein the at least one period after the treatment is a plurality of periods, and at least one of the periods is partially overlapped with a recommend follow-up time point.

9. The method according to claim 8, wherein the recommend follow-up time point is 6 months after the treatment, 12 months after the treatment, 18 months after the treatment, or 24 months after the treatment.

10. The method according to claim 8, wherein a duration of the periods is 1 month, 2 months, 3 months, 4 months, 5 months, or 6 months.

* * * * *